United States Patent [19]

Petersen

[11] 4,332,611

[45] Jun. 1, 1982

[54] HERBICIDAL SULFONAMIDES

[75] Inventor: Wallace C. Petersen, Hockessin, Del.

[73] Assignee: E. I. Du Pont de Nemours and Company, Wilmington, Del.

[21] Appl. No.: 259,981

[22] Filed: May 12, 1981

Related U.S. Application Data

[63] Continuation-in-part of Ser. No. 168,352, Jul. 11, 1980, abandoned.

[51] Int. Cl.$^3$ .................... A01N 43/54; A01N 43/66
[52] U.S. Cl. ........................................... 71/92; 71/93; 544/211; 544/253; 544/278; 544/321; 544/332

[58] Field of Search .................. 71/92, 93; 544/211, 544/253, 278, 321, 332

[56] References Cited

U.S. PATENT DOCUMENTS 4,257,802  3/1981  Levitt ...................................... 71/93

Primary Examiner—Paul M. Coughlan, Jr.

[57]  ABSTRACT

Hydroxymethylbenzenesulfonamide derivatives have utility as agricultural chemicals and in particular as herbicides.

25 Claims, No Drawings

HERBICIDAL SULFONAMIDES

CROSS-REFERENCE TO RELATED APPLICATIONS

This application is a continuation-in-part of my co-pending application Ser. No. 168,352, filed July 11, 1980, now abandoned.

BACKGROUND OF THE INVENTION

This invention relates to hydroxymethylbenzenesulfonamide derivatives which are useful as agricultural chemicals and in particular as general herbicides having both pre- and post-emergence activity.

Netherlands Pat. No. 121,788, published Sept. 15, 1966, discloses the preparation of compounds of the following Formula and their use as general or selective herbicides:

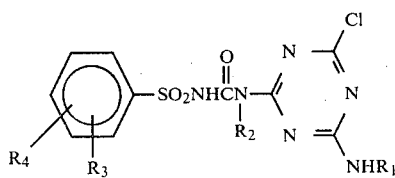

wherein
$R_1$ and $R_2$ may independently be alkyl of 1-4 carbon atoms; and
$R_3$ and $R_4$ may independently be hydrogen, chlorine or alkyl of 1-4 carbon atoms.

U.S. Pat. No. 3,637,366 discloses compounds having the formula:

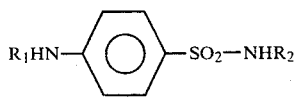

wherein
$R_1$ is hydrogen or lower saturated aliphatic acyl and
$R_2$ is hydrogen, 2-pyrimidinyl, pyridyl, amidino, acetyl or carbamoyl.
The disclosed compounds are said to provide control of crabgrass, cress, endive, clover and *Poa annua*.

French Pat. No. 1,468,747 discloses the following para-substituted phenylsulfonamides as being useful as antidiabetic agents:

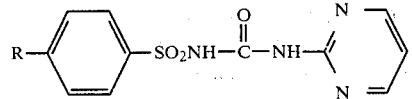

wherein R=H, halogen, $CF_3$ or alkyl.

Logemann et al. Chem Ab., 53, 18052 g (1969), disclose a number of sulfonamides, including uracil derivatives and those having the formula:

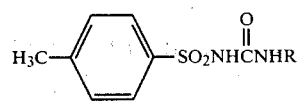

wherein
R is butyl, phenyl, or

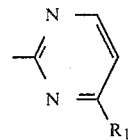

and
$R_1$ is hydrogen or methyl.
When tested for hypoglycemic effect in rats (oral doses of 25 mg/100 g), the compounds in which R is butyl and phenyl were most potent. The others were of low potency or inactive.

Wojciechowski, J. Acta. Polon. Pharm 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

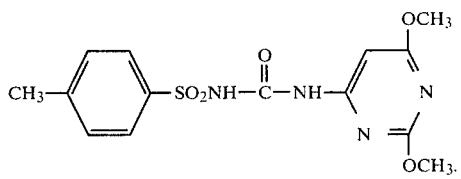

Based upon similarity to a known compound, the author speculated that the foregoing compound might have a hypoglycemic activity.

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959]:

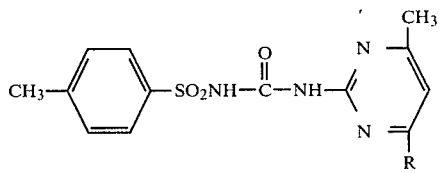

wherein R=H or $CH_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. A wide variety of materials useful for killing or inhibiting (controlling) the growth of undesired vegetation is available; such materials are commonly referred to as herbicides. The need still exists however, for more effective herbicides.

SUMMARY OF THE INVENTION

This invention relates to novel compounds of Formula I and their agriculturally suitable salts, suitable agricultural compositions containing them, and their method of use as general and selective preemergence and post-emergence herbicides and as plantgrowth regulants.

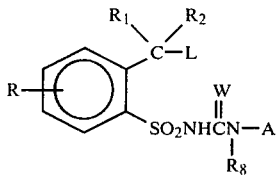 (1)

wherein
L is OH, OC(O)R$_{11}$, OC(O)NHR$_{12}$ or OC(O)OR$_{13}$;
R is H, F, Cl, Br, NO$_2$, CF$_3$, C$_1$–C$_3$ alkyl or C$_1$–C$_3$ alkoxy;
R$_1$ is H or C$_1$–C$_4$ alkyl;
R$_2$ is H or CH$_3$;
R$_8$ is H, CH$_3$ or OCH$_3$;
R$_{11}$ is H, C$_1$–C$_5$ alkyl, C$_2$–C$_3$ alkenyl, C$_2$–C$_3$ alkynyl, C$_3$–C$_4$ cycloalkyl,

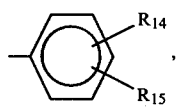

C$_1$–C$_4$ alkyl substituted with 1–4 substituents selected from 0–3 F., 0–3 Cl or 0–3 Br, or C$_2$–C$_3$ alkenyl substituted with 1–3 Cl;
R$_{12}$ is H, C$_1$–C$_6$ alkyl, C$_3$–C$_4$ alkenyl, C$_5$–C$_6$ cycloalkyl,

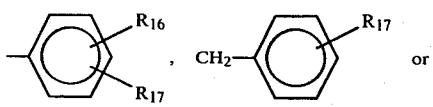

C$_5$–C$_6$ cycloalkyl substituted with CH$_3$;
R$_{13}$ is C$_1$–C$_6$ alkyl or

R$_{14}$ and R$_{15}$ are independently H, NO$_2$, CH$_3$, Cl or OCH$_3$;
R$_{16}$ is H, F, Cl, Br, C$_1$–C$_3$ alkyl, NO$_2$, CN, SO$_2$CH$_3$, OCH$_3$, SCH$_3$ or CF$_3$;
R$_{17}$ H, Cl or C$_1$–C$_3$ alkyl;
R$_{18}$ is H, CH$_3$ or Cl;
A is

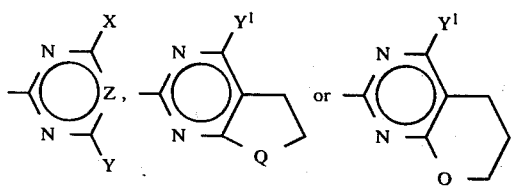

W is O or S;
X is H, Cl, Br, CH$_3$, CH$_2$CH$_3$, C$_1$–C$_3$ alkoxy, CF$_3$, SCH$_3$ or CH$_2$OCH$_3$;
Y is CH$_3$ or OCH$_3$;
Z is N, CH, CCl, CBr, CCN, CCH$_3$, CCH$_2$CH$_3$, CCH$_2$CH$_2$Cl or CCH$_2$CH=CH$_2$;
Y$^1$ is H, CH$_3$, OCH$_3$ or OCH$_2$CH$_3$; and Q is O or CH$_2$;
and their agriculturally suitable salts; provided that when W is S, then R$_8$ is H.

Preferred Compounds

Preferred for their higher activity and/or more favorable ease of sytnthesis are:
(1) Compounds of the generic scope where Z is N, CH, CCl, CBr or CCH$_3$, W is O and R$_8$ is H or CH$_3$.
(2) Compounds of the generic scope where L is OH, R is H, R$_1$ and R$_2$ are CH$_3$, R$_8$ is H or CH$_3$; A is

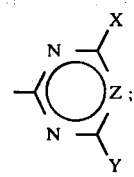

Z is CH or N; X and Y are independently CH$_3$ or OCH$_3$; and W is O;
(3) Compounds of Preferred (1) where Z is CH or N; X is CH$_3$ or OCH$_3$; and R$_1$ is H or CH$_3$;
(4) Compounds of Preferred (3) where R and R$_8$ are H, and A is

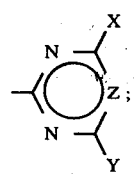

(5) Compounds of Preferred (4) where R$_{11}$, R$_{12}$ and R$_{13}$ are C$_1$–C$_3$ alkyl;
(6) Compounds of Preferred (4) where L is OH.
Specifically preferred for their highest activity and/or most favorable ease of synthesis are:
N-[(4,6-Dimethoxypyrimidin-2-yl)aminocarbonyl]-2-(hydroxymethyl)benzenesulfonamide, mp 149°–151°;
N-[(4,6-Dimethoxy-1,3,5-triazin-2-yl)aminocarbonyl]-2-(hydroxymethyl)benzenesulfonamide, mp 146°–148° (d);
N-[(4,6-Dimethylpyrimidin-2-yl)aminocarbonyl]-2-(hydroxymethyl)benzenesulfonamide;
N-[(4-methoxy-6-methylpyrimidin-2-yl)aminocarbonyl]-2-(hydroxymethyl)benzenesulfonamide;
N-[(4,6-Dimethyl-1,3,5-triazin-2-yl)aminocarbonyl]-2-(hydroxymethyl)benzenesulfonamide; and
N-[(4-Methoxy-6-methyl-1,3,5-triazin-2-yl)aminocarbonyl]-2-(hydroxymethyl)benzenesulfonamide.

DETAILED DESCRIPTION OF THE INVENTION

Synthesis

Many of the compounds of Formula I may be prepared as shown in Equation 1 by reaction of an appropriately substituted o-hydroxymethylbenzenesulfonylurea, II, with an appropriate acid chloride.

Equation 1

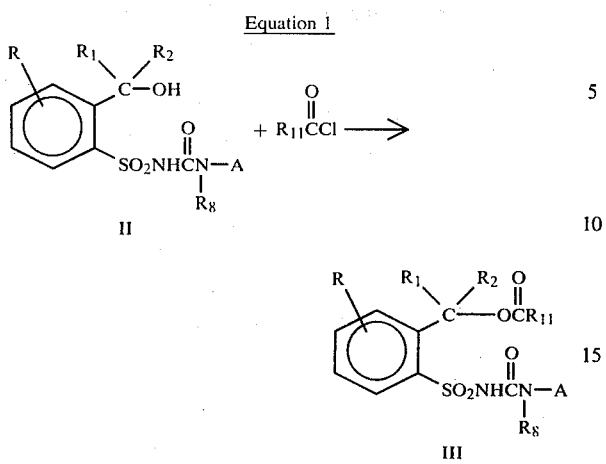

The reaction of Equation 1 is best carried out in inert aprotic solvents such as methylene chloride, tetrahydrofuran or acetonitrile at 0°–80° C. An excess of the acid chloride is used and at least one equivalent of a tertiary amine such as pyridine, triethylamine or 4-dimethylaminopyridine. Isolation is achieved by evaporation of solvent and recrystallization from suitable solvents such as 1-chlorobutane, ethyl acetate or ethyl ether or by column chromatography over silica gel.

Other compounds of Formula I may be prepared as shown in Equation 2 by reaction of an appropriately substituted o-hydroxymethylbenzenesulfonylurea, II, with an appropriate isocyanate.

Equation 2

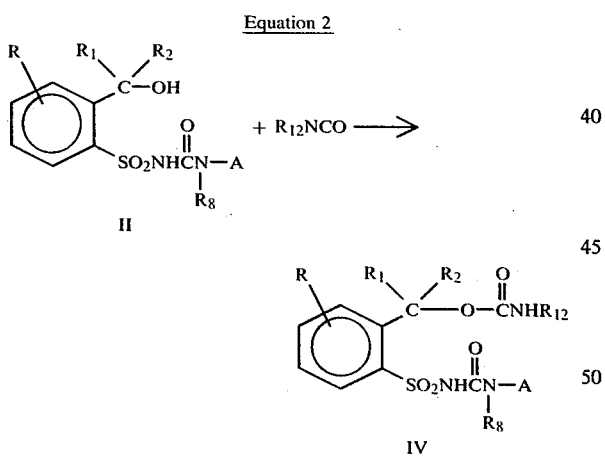

The reaction of Equation 2 is best carried out in inert aprotic solvents such as methylene chloride, tetrahydrofuran or acetonitrile at 0°–80° C. An excess of the isocyanate is used and a catalyst such as dibutyltindilaurate or 1,4-diaza[2,2,2]bicyclooctane (DABCO). Isolation is achieved by evaporation of solvent and recrystallization from suitable solvents such as 1-chlorobutane, ethyl acetate or ethyl ether or by column chromatography over silica gel.

Other compounds of Formula I may be prepared as shown in Equation 3 by reaction of an appropriately substituted o-hydroxymethylbenzenesulfonylurea, II, with an appropriate chloroformate.

Equation 3

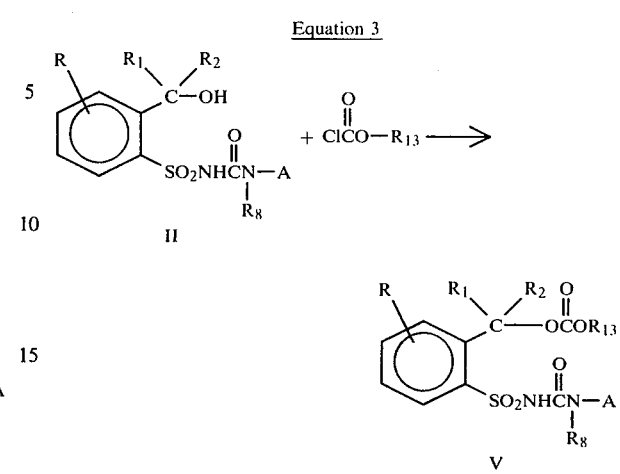

The reaction of Equation 3 is best carried out in inert aprotic solvents such as methylene chloride, tetrahydrofuran or acetonitrile at 0°–80° C. An excess of the chlorocarbonate is used and at least one equivalent of a tertiary amine such as pyridine, triethylamine or 4-dimethylaminopyridine. Isolation is achieved by evaporation of solvent and recrystallization from suitable solvents such as 1-chlorobutane, ethyl acetate or diethyl ether or by column chromatography over silica gel.

The preparation of compounds of Formula II where $R_1=R_2=H$ may be prepared as shown in Equation 4.

Equation 4

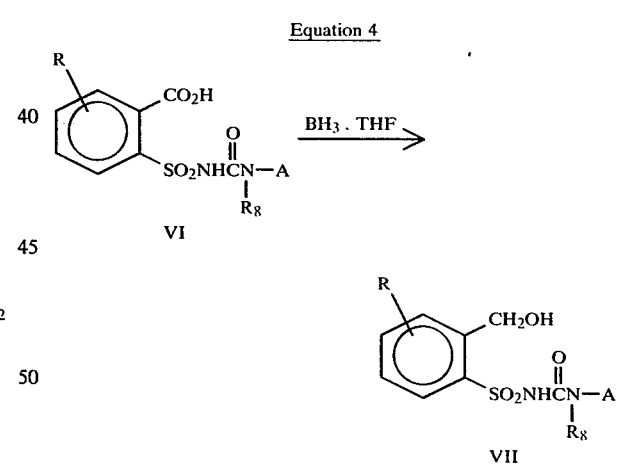

The carboxylic acid, VI, may be converted to the alcohol by reduction with 4–5 equivalents of borane-THF reagent in THF at ambient pressure and temperature for 4 to 18 hours. Isolation is achieved by drowning in dilute acid followed by extraction of the product with a solvent such as methylene chloride, ethyl acetate or ethyl ether. Evaporation of solvent and crystallization of column chromatography on silica gel affords the pure alcohol, VII.

The carboxylic acids, VI, may be prepared by hydrolysis of the corresponding methyl esters as shown in Equation 5.

Equation 5

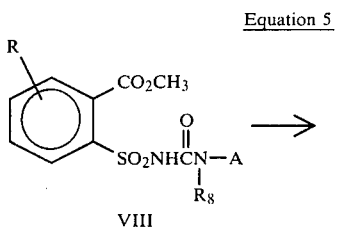

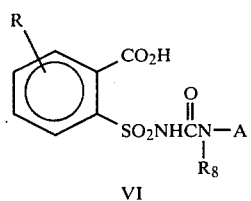

When A is a pyrimidine type structure, the methyl esters are best hydrolyzed by dissolving in a solution of 80 parts ethanol, 10 parts water and 10 parts potassium hydroxide. The mixture is stirred at ambient temperature for 18 hours followed by pouring into a large excess of water and acidifying to a pH of 2.0. The pure acid, VI, precipitates and is filtered and washed with water.

When A is a triazine and X or Y is alkoxy, the hydrolysis is best performed by dissolving the ester in a solution of potassium t-butoxide in dimethyl sulfoxide at ambient temperature for two hours. Addition of a large volume of water followed by acidification to a pH of 2.0 precipitates the acid, VI.

The preparation of esters of Formula VIII is described in European Patent Application 7687.

Compounds of Formula VII may also be prepared by treatment of the carboxylic acids, VI, or the methyl esters, VIII, with lithium aluminum hydride by the procedures described by R. F. Nystrom and W. G. Brown, J. Am. Chem. Soc. 69, 2548 (1947) and R. B. Moffett, *Organic Synthesis*, Coll. Vol. 4, 834 (1963). Reduction of the esters with sodium bis(2-methoxyethoxy)aluminum hydride is described in M. Fieser and L. E. Fieser, *Reagents for Organic Synthesis*, John Wiley & Sons, New York, Vol. 5, p. 596 (1975).

The preparation of compounds of Formula II where $R_1=H$ and $R_2=CH_3$ may be carried out as shown in Equation 6.

Equation 6

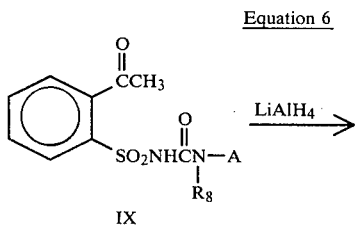

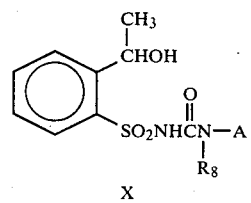

Compounds of Formula IX are treated with one equivalent of lithium aluminum hydride (LAH) in a solvent such as ether, tetrahydrofuran or glyme at $-20°$ to 25° C. for 1 to 6 hours. Next there is a successive dropwise addition of an equivalent number of ml of water as grams of LAH followed by an equal number of ml of 15% sodium hydroxide followed by 3 times that number of ml of water. This produces a dry granular precipitate of aluminum oxide which is easy to filter. The aqueous phase is then acidified with dilute acid and the product extracted with solvent such as methylene chloride, ethyl acetate or ethyl ether. Evaporation of solvent and crystallization or column chromatography on silica gel affords the pure alcohol, X.

Compounds of Formula IX are prepared by the reaction, as shown in Equation 7, using an excess of methyl lithium with a carboxylic acid derivative of Formula VI.

Equation 7

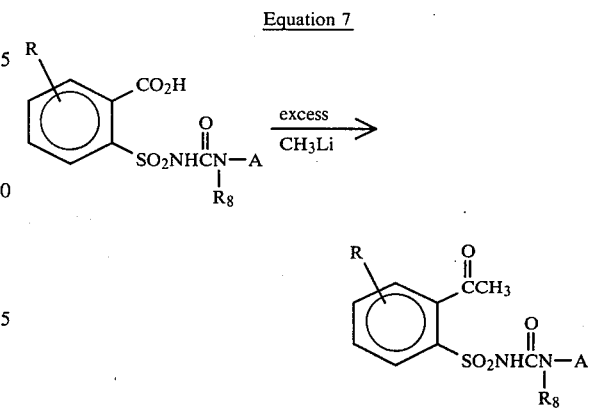

Compounds of Formula VI are restricted to structures in which the substituents R, Z, X and Y contain no displaceable halogens, $NO_2$ or CN.

An excess of methyl lithium in a suitable solvent such as diethyl ether, hexane, pentane or benzene is added to a solution or slurry of VI in a similar solvent at temperatures between $-100°$ and 0° C. The mixture is allowed to warm to room temperature and stir for 30 minutes. Aqueous acid is then added and the compound IX is extracted into a suitable solvent to free it from salts, followed by evaporation of the solvent. Purification is by chromatography on silica gel.

Another procedure for the preparation of compounds of Formula X is the reaction of excess methyl lithium with the corresponding aldehyde XI as shown in Equation 8.

Equation 8

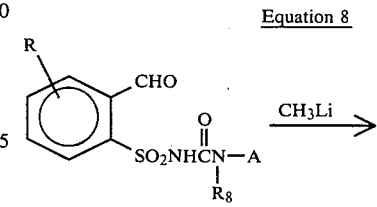

Equation 8 (continued)

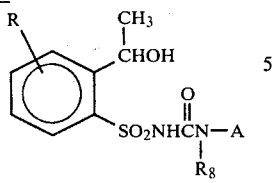

Compounds of Formula XI are restricted to structures in which the substituents R, Z, X and Y contain no displaceable halogens; $NO_2$ or CN.

An excess of methyl lithium in a suitable solvent such as diethyl ether, hexane, pentane or benzene is added to a solution or slurry of XI in a similar solvent at temperatures between $-100°$ and $0°$ C. The mixture is allowed to warm to room temperature and stir for 30 minutes. Aqueous acid is then added and the compound X is extracted into a suitable solvent to free it from salts followed by evaporation of the solvent. Purification is by chromatography on silica gel.

Aldehydes of Formula XI are prepared by the procedure of Equation 9.

Equation 9

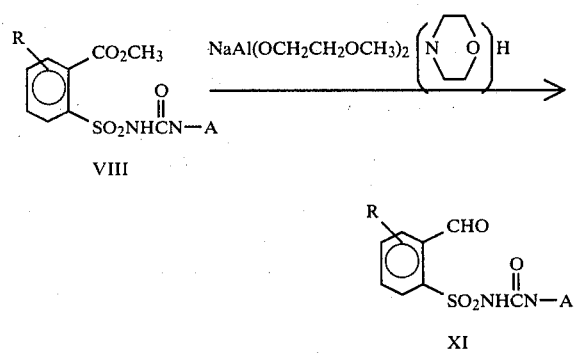

Following the procedure of R. Kanayawa and T. Tokoroyama, a solution of sodium bis(2-methoxyethoxy)aluminum hydride in THF is reacted with one equivalent of morpholine. To this solution at $-40°$ C. is added methyl ester of Formula VIII and the solution is allowed to warm to $25°$ C. The product is isolated by addition of aqueous acid and extraction into ether or methylene chloride. Evaporation of solvent and crystallization of column chromatography on silica gel affords the pure aldehyde, XI.

Aldehydes of Formula XI may also be prepared from the esters of Formula VIII by treatment with diisobutylaluminum hydride according to procedures of E. Winterfeldt, Synthesis, 617 (1975).

The preparation of compounds of Formula II where $R_1=R_2=CH_3$ may be prepared as shown in Equation 10.

Equation 10

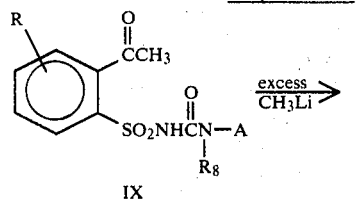

Equation 10 (continued)

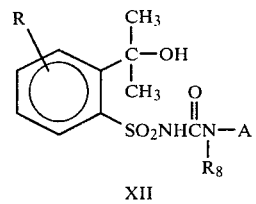

Compounds of Formula XII are prepared by the reaction of an excess of methyl lithium with acetophenones of Formula IX.

Compounds of Formula IX are restricted to structures in which the substituents R, Z, X and Y contain no displaceable halogens, $NO_2$ or CN.

An excess of methyl lithium in a suitable solvent such as diethyl ether, hexane, pentane or benzene is added to a solution or slurry of IX in a similar solvent at temperatures between $-100°$ and $0°$ C. The mixture is allowed to warm to room temperature and stir for 30 minutes. Aqueous acid is then added and the compound XII is extracted into a suitable solvent to free it from salts followed by evaporation of the solvent. Purification is by chromatography on silica gel.

Some of the compounds of Formula I, where Z is CH or N, can also be prepared by the method described in Equation 11.

Equation 11

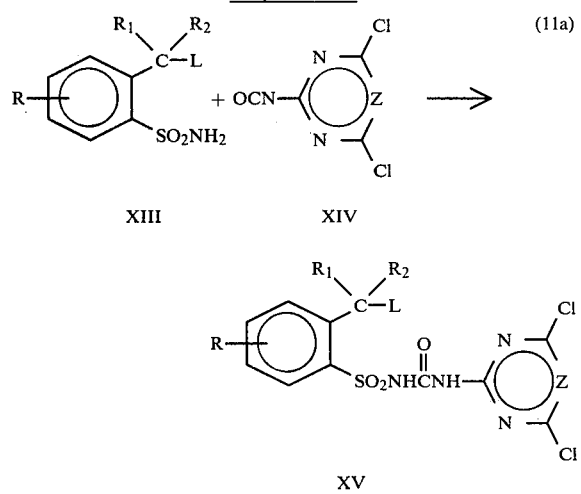

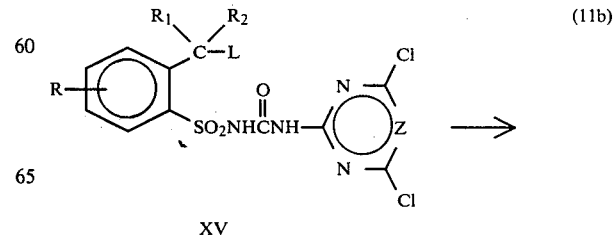

-continued
Equation 11

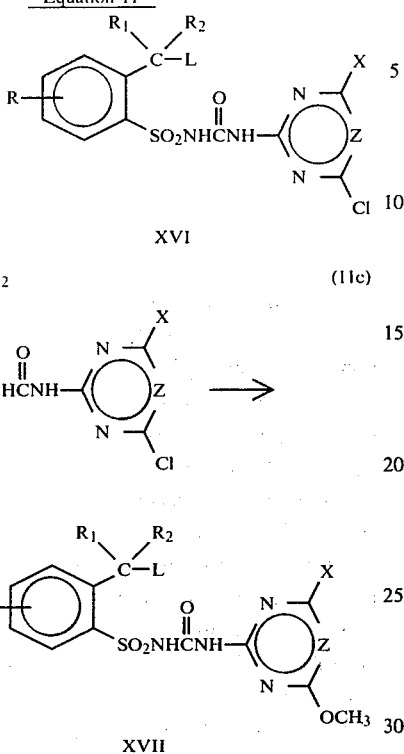

wherein R, $R_1$ and $R_2$ are as described in Formula I, X is $C_1$-$C_3$ alkoxy and L is not OH.

Reaction Step (11a)

In Reaction Step (11a), an aromatic sulfonamide of Formula XIII is contacted with a heterocyclic isocyanate of Formula XIV to yield an N-(haloheterocyclicaminocarbonyl)aromatic sulfonamide of Formula XV.

The heterocyclic isocyanates used in Reaction (11a) may be prepared according to methods described in Swiss Pat. No. 579,062, U.S. Pat. No. 3,919,228, U.S. Pat. No. 3,732,223 and *Angew Chem. Int. Ed.* 10, 402 (1976), the disclosures of which are herein incorporated by reference.

The aromatic sulfonamide and the heterocyclic isocyanate are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110° C., and the product can generally be recovered by cooling and filtering the reaction mixture. For reasons of efficiency and economy, the preferred solvents are acetonitrile and THF, and the preferred temperature range is about 60° to 85° C.

Reaction Steps (11b) and (11c)

In Reaction Steps (11b) and (11c), one or two of the halogen atoms on the heterocyclic ring of the compound of Formula XV is displaced by a nucleophilic species. Generally, this may be done by contacting the compound of Formula XV either with alkanol or with alkoxide as described by X where X is $C_{1-3}$ alkoxy.

Thus, in Reaction Step (11b), a compound of Formula XV, substituted with one displaceable group can be contacted with at least one equivalent of alkanol. This reaction is sluggish, however, and it is preferred to contact the compound of Formula XV with at least two equivalents of alkoxide. The alkoxide can be provided in a number of ways.

(a) The compound of Formula XV can be suspended or dissolved in an alkanol solvent in the presence of at least two equivalents of alkoxide. The alkoxide can be added directly as alkali metal or alkaline earth metal alkoxide or can be generated by the addition to the alkanol solvent of at least two equivalents of a base capable of generating alkoxide from the solvent. Suitable bases include, but are not limited to, the alkali and alkaline earth metals, their hydrides and tert-butoxides. For example, when X is methoxy, the compound of Formula XV could be suspended or dissolved in methanol in the presence of two equivalents of sodium methoxide. Alternatively, two equivalents of sodium hydride could be used in place of the sodium methoxide.

(b) The compound of Formula XV can be suspended or dissolved in an inert solvent in the presence of at least two equivalents of alkoxide. Suitable inert solvents include, but are not limited to, acetonitrile, THF and dimethylformamide. The alkoxide may be added directly as alkali metal or alkaline earth metal alkoxide or may be generated from alkanol and a base as described in (a) above. For example, when X is methoxy, the compound of Formula XV could be suspended or dissolved in THF in the presence of two equivalents of sodium methoxide. Alternatively, two equivalents each of methanol and sodium hydride could be used instead of sodium methoxide.

For reasons of economy and efficiency, procedure (a) is the more preferred method.

It should be noted that two equivalents of alkoxide are required for Reaction Step (b) whereas only one equivalent of alkanol is needed for the same process. This difference is due to the reaction which is believed to occur between the alkoxide and the sulfonyl nitrogen of the sulfonamide of Formula XV. When alkoxide is used, the first equivalent of alkoxide removes a proton from the sulfonyl nitrogen, and is only the second equivalent which effects displacement of the halogen. As a result, two equivalents of alkoxide are required. The resulting salt must be acidified, e.g., with sulfuric, hydrochloric or acetic acid, to yield a compound of Formula XVI. Applicant, of course, does not intend to be bound by the mechanism described above.

In Reaction Step (11c) a compound of Formula XVI, is contacted with either one equivalent of methanol or with two equivalents of methoxide. When methoxide is used, it may be provided in either of the methods described above in connection with Reaction Step (11b) and the resulting salt can be acidified to yield a compound of Formula XVII.

When X=$OCH_3$, Reaction Steps (11b) and (11c) may be combined. Thus, a compound of Formula XV may be contacted either with at least two equivalents of methanol or with at least three equivalents of methoxide.

For a compound of Formula XV, certain reaction conditions will favor displacement of only one of the chlorine groups. These conditions are the use of low temperatures and, when alkoxide is used, the slow addition of the stoichiometric amount of alkoxide or alkoxide-generating base to the medium containing the compound of Formula XV.

When alkoxide is used, both Reaction Steps (11b) and (11c) are preferably run at temperatures within the range of about $-10°$ C., the range of about $0°$ to $25°$ C. being more preferred. Reaction Steps (11b) and (11c) are more sluggish when alkanol is used instead of alkoxide, and more drastic conditions are required for the reaction to go to completion. Thus, higher temperatures, up to and including the boiling point of the alkanol itself, are required.

Depending on the nature of L in the compounds of Formula XIII, the conversion to compounds of Formula XVII by the reactions described in Equation 11 is carried out without alteration of L. In other cases, the reactions result in the hydrolysis of the benzyl alcohol derivatives to give compounds of Formula XVIII wherein L is OH. Other compounds of Formula I may then be prepared by the methods previously described.

Thus, the reaction sequence described in Equation 12 shows a protected 2-hydroxymethylbenzenesulfonamide converted to a useful herbicide via reaction with a heterocyclic isocyanate.

Equation 12

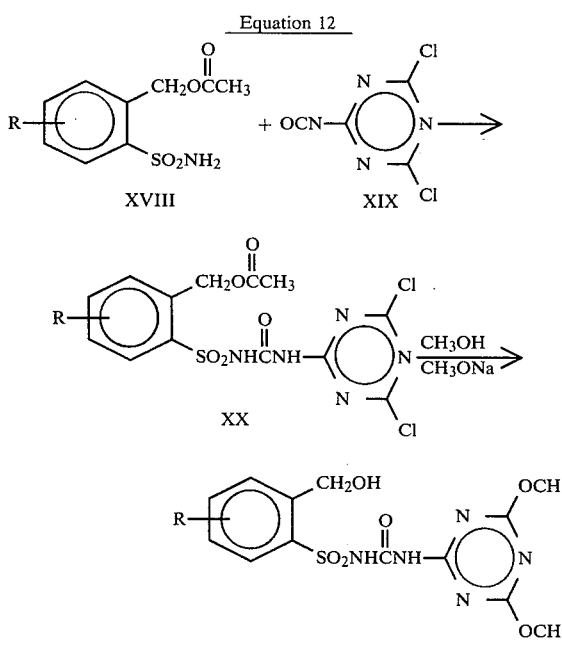

As shown in Equation 13, compounds of Formula I wherein W is S are prepared by the reaction of an appropriately substituted benzenesulfonamide with the appropriate triazine or pyrimidine isothiocyanate of formula XXI.

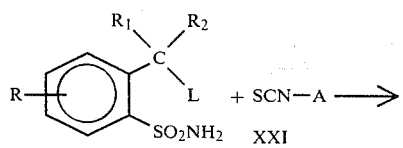

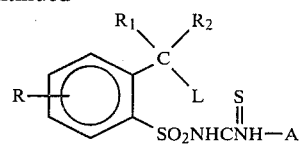

The reaction of Equation 13 is best carried out by dissolving or suspending the sulfonamide and isothiocyanate in a polar solvent such as acetone, acetonitrile, ethyl acetate or methylethylketone, adding an equivalent of a base such as potassium carbonate and stirring the mixture at ambient temperature up to the reflux temperature for 1 to 24 hours. In some cases, the product precipitates from the reaction mixture and can be removed by filtration. The product is stirred in dilute mineral acid, filtered and washed with cold water. If the product does not precipitate from the reaction mixture, it can be isolated by evaporation of the solvent, trituration of the residue with dilute mineral acid and filtering off the insoluble product.

The heterocyclic isothiocyanates which are used in the procedure of Equation 13 are prepared, for example, according to the method of Japan patent Application Pub.: Kokai No. 51-143686, June 5, 1976, or that of W. Abraham and G. Barnikow, *Tetrahedron*, 29, 691-697 (1973).

From the above, it is seen that compounds of Formula XX are useful intermediates in the preparation of compounds of this invention.

Compounds of Formula XVIII can be prepared via a series of standard functional group transformations as (J. F. King, A. Hawson, B. L. Huston, L. J. Danks, and J. Komery, Can. J. Chem. 49, 943 (1971) for 2-(chloromethyl)benzenesulfonyl chloride.

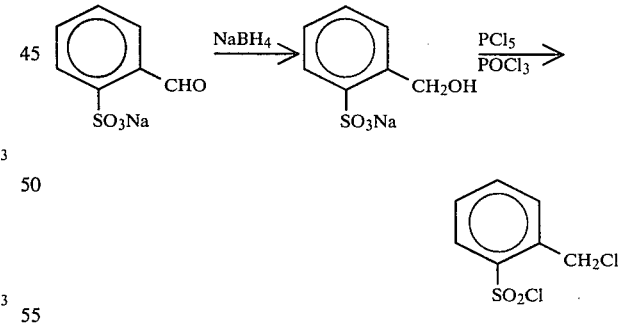

Conversion of sulfonyl chlorides to sulfonamides is well known, e.g., Crossley et al., J. Am. Chem. Soc., 60, 2223 (1938).

For those examples containing reactive functionality on the position ortho to the sulfonamide moiety it is convenient to add the sulfonyl chloride to a measured quantity of ammonia in an inert solvent, e.g., tetrahydrofuran, ethyl acetate, etc. at low temperatures ($-78°$-$0°$). Side reactions such as ring formation, elimination or condensation are thereby substantially avoided.

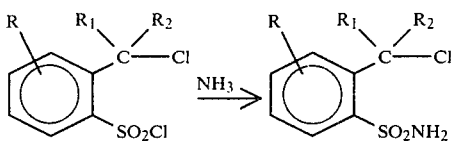

The α-haloalkylbenzenesulfonamide may be converted to other required intermediates for this invention by treatment which appropriate nucleophiles, e.g., acetate ion as described in Example 4.

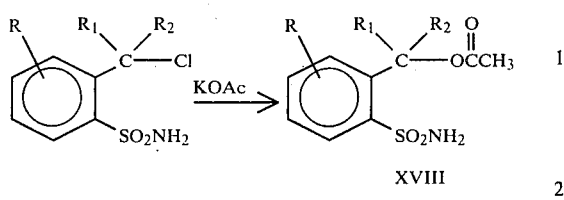

XVIII

Thus, compounds of Formula XVIII are useful intermediates in the preparation of compounds of this invention.

The synthesis of heterocyclic amines has been reviewed in "The Chemistry of Heterocyclic Compounds" a series published by Interscience Publ., New York and London. 2-Aminopyrimidines are described by D. J. Brown in The Pyrimidines, Vol. XVI of this series. The 2-amino-1,3,5-triazines are reviewed by K. R. Huffman and in The Triazines of this same series. The synthesis of triazines are also described by F. C. Schaefer, U.S. Pat. No. 3,154,547 and by K. R. Huffman and F. C. Schaeffer, J. Org. Chem. 28, 1816–1821 (1963).

The preparation of the aminoheterocycles described by the following formulae are prepared by methods described in unexamined European Pat. No. 15683.

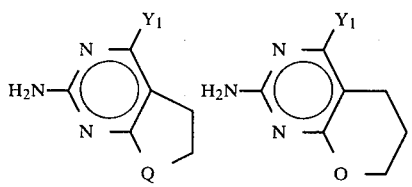

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

N-[(4,6-Dimethoxypyrimidin-2-yl)aminocarbonyl]-2-carboxybenzenesulfonamide

A mixture containing 5 g of N-[(4,6-dimethoxypyrimidin-2-yl)aminocarbonyl]-2-methoxycarbonylbenzenesulfonamide, 20 ml of ethanol, 2.5 ml of water and 2.5 g of potassium hydroxide was stirred at ambient temperature and pressure for 18 hours. The mixture was then diluted with 250 ml of water and 20 ml of concentrated hydrochloric acid was added with stirring. The precipitate was filtered and washed with water and dried to yield 4.85 g of the desired product, melting at 161°–2° C. The infrared absorption peaks at 3500, 3400 and 1700 cm$^{-1}$ are consistent with the desired structure and the nuclear magnetic resonance absorption peaks at 3.95 ppm, S, 6H, OCH$_3$ of pyrimidine; 5.8 ppm S, 1H, pyrimidine proton at position 5; and 7.6–8.3 ppm, M, 4H, aromatic protons, are consistent with the desired structure.

EXAMPLE 2

N-[(4,6-Dimethoxypyrimidin-2-yl)aminocarbonyl]-2-(hydroxymethyl)benzenesulfonamide To a solution of 3.9 g of N-[(4,6-dimethoxypyrimidin-b 2-yl)aminocarbonyl]-2-carboxybenzenesulfonamide in 100 ml of tetrahydrofuran was added 50 ml of a 1 M solution of borane, THF complex at 25° C. The mixture was stirred at 25° C. for 18 hours followed by addition of water and HCl. The mixture was extracted with methylene chloride and the desired product crystallized from solution, 1.1 g 29% yield, m.p. 149°–150° C. The infrared absorption peaks at 3300 cm$^{-1}$ and 1720 cm$^{-1}$ are consistent with the desired structure and the nuclear magnetic resonance absorption peaks at 3.95 ppm, S, 6H, OCH$_3$ of pyrimidine; 4.9 ppm, S, 2H, benzyl protons; 5.9 ppm, S, 1H, pyrimidine proton at position 5; and 7.4–8.3 ppm, Multiplet, 4H, aromatic protons are consistent with the desired structure.

EXAMPLE 3

N-[(4,6-Dimethoxypyrimidin-2-yl)aminocarbonyl]-2-methylcarbonylbenzenesulfonamide A mixture containing 0.85 g of N-[(4,6-dimethoxypyrimidin-2-yl)aminocarbonyl]-2-carboxybenzenesulfonamide in 50 ml of anhydrous tetrahydrofuran was treated with 40 ml of 1.4 molar solution of methyl lithium (low halide, Aldrich) in ether at 25° under a nitrogen atmosphere. The mixture was stirred for 4 hours at 25° and was then poured into 500 ml of water containing 10 ml of concentrated hydrochloric acid. The precipitated oil was extracted into methylene chloride and the oil on evaporation of solvent was purified by preparative thin layer chromatography on silica gel (Analtec, 2000 micron, 20×20 plates) by elution with ethyl acetate/hexane in a one to one ratio. The isolated product was recrystallized from a 1-chlorobutane and hexane mixture to give 0.1 g, m.p. 126°-8°. The infrared absorption showed a broadened carbonyl peak at 1710 cm$^{-1}$, and the absence of the 3500 and 3400 cm$^{-1}$ peaks of the starting material. The nuclear magnetic resonance spectrum showed peaks at 2.6 ppm S, 3H,

4.0 ppm, S, 6H, CH$_3$O of pyrimidine; 5.7 ppm S, 1H, pyrimidine proton at position 5; and 7.3-7.7 ppm and 8.0 ppm M, 4H, aromatic, which are constitent with the desired structure.

EXAMPLE 4

N-[(4,6-Dimethoxypyrimidin-2-yl)aminocarbonyl]-2-(α-hydroxyethyl)benzenesulfonamide A mixture containing 1.0 g of N-[(4,6-dimethoxypyrimidin-2-yl)aminocarbonyl]-2-methylcarbonylbenzenesulfonamide in 50 ml of anhydrous THF is treated with 0.1 g of lithium aluminum hydride at 25° under a nitrogen atmosphere. The mixture is stirred for 4 hours at 25° and is then poured into 500 ml of water containing 10 ml of concentrated hydrochloric acid. The precipitated oil is extracted into methylene chloride and the solid on evaporation is purified by column chromatography on silica gel.

EXAMPLE 5

2-(Acetoxymethyl)benzenesulfonamide

A mixture of 2-(chloromethyl)benzenesulfonamide (2.00 g), potassium acetate (6.0 g) and water (75 ml) was heated to reflux for 1.5 hour. The pH was adjusted to ca. 5.0 by addition of hydrochloric acid and the chilled mixture was filtered to give 1.05 of of shiny white solid, m.p. 131°-133°. 'H NMR δ(CD$_3$)$_2$CO 8.00-7.83 (M), 7.60-7.25 (M), 6.55 (brd s), 5.47 (s), 2.97 (brd s), 2.10 (s), consistent with the assigned structure.

EXAMPLE 6

2-(Acetoxymethyl)-N-[(4,6-dichloro-1,3,5-triazin-2-yl)aminocarbonyl]benzenesulfonamide A solution of 4,6-dichloro-1,3,5-triazin-2-yl isocyanate (0.87 g, 4.5 mmol) in acetonitrile (9 ml) was treated with 2-(acetoxymethyl)benzenesulfonamide (1.04 g, 4.5 mmol) and stirred for 16 hours. Volatiles were removed under vacuum to give a residue whose 'H NMR showed δ(CD$_3$)$_2$CO, 8.05-7.80 (m, 1H), 7.65-7.27 (m, 3H), 6.45 (brd s, 1H), 5.50 (s, 2H), 2.10 (s, 3H), consistent with the assigned structure.

EXAMPLE 7

2-(Hydroxymethyl)-N-[(4,6-dimethoxy-1,3,5-triazin-2-yl)aminocarbonyl]benzenesulfonamide The crude 2-(acetoxymethyl)-N-[(4,6-dichloro-1,3,5-triazinyl)aminocarbonyl]benzenesulfonamide was treated with methanol (10 ml) and then with a solution of sodium methoxide (14 mmol) in methanol. The mixture was stirred at room temperature for 1.5 hour and evaporated. The residue was taken up in water and filtered. The filtrate was acidified and filtered to give 0.45 g of gummy solid which was recrystallized from a chloroform/acetone mixture to give 115 mg of white solid, m.p. 146°-148°(dec.). 'H NMR δDMSO-d$_6$ 12.2(brd s, 1H), 10.73 (s, 1H), 8.00-7.15 (m,4H), 4.80 (s and ~4.9-4.2 (brd s), 3H) 3.90 (s, 6H), consistent with the assigned structure.

Using the procedures of Examples 1 to 7 and the proper reactants or the methods described herein, the compounds of Tables I–XII may be prepared.

TABLE I

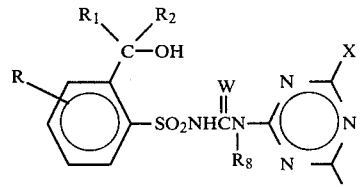

| R | R$_1$ | R$_2$ | W | R$_8$ | X | Y | m.p.(°C.) |
|---|---|---|---|---|---|---|---|
| H | H | H | O | H | CH$_3$ | CH$_3$ | |
| H | H | H | O | H | OCH$_3$ | CH$_3$ | |
| H | H | H | O | H | OCH$_3$ | OCH$_3$ | |
| H | H | CH$_3$ | O | H | CH$_3$ | OCH$_3$ | |
| H | H | CH$_3$ | O | H | SCH$_3$ | OCH$_3$ | |
| H | CH$_3$ | CH$_3$ | O | H | CH$_3$ | OCH$_3$ | |
| H | CH$_3$ | CH$_3$ | O | H | OCH$_3$ | OCH$_3$ | |
| 5-F | H | H | O | H | CH$_3$ | CH$_3$ | |
| 6-F | H | H | O | H | OCH$_3$ | OCH$_3$ | |
| 5-Cl | H | H | O | H | CH$_3$ | OCH$_3$ | |
| 3-Cl | H | H | O | H | OCH$_3$ | CH$_3$ | |
| 5-NO$_2$ | H | H | O | H | CH$_3$ | OCH$_3$ | |
| 5-NO$_2$ | H | H | O | H | OCH$_3$ | OCH$_3$ | |
| 5-OCH$_3$ | H | H | O | H | CH$_3$ | OCH$_3$ | |
| 5-OCH$_3$ | H | H | O | H | OCH$_3$ | OCH$_3$ | |
| 4-CF$_3$ | H | H | O | H | CH$_3$ | OCH$_3$ | |
| 5-CF$_3$ | H | H | O | H | OCH$_3$ | OCH$_3$ | |
| 5-CH(CH$_3$)$_2$ | H | H | O | H | OCH$_3$ | CH$_3$ | |
| OCH$_2$CH$_2$CH$_3$ | H | H | O | H | CH$_3$ | OCH$_3$ | |
| 4-CH$_3$ | H | H | O | H | CH$_3$ | | |
| 5-CH$_3$ | H | H | O | H | OCH$_3$ | O | |
| H | H | H | O | H | Cl | Cl | |
| 5-CH$_3$ | H | H | O | H | Cl | Br | |

TABLE I-continued

| R | R$_1$ | R$_2$ | W | R$_8$ | X | Y | m.p.(°C.) |
|---|---|---|---|---|---|---|---|
| H | CH$_3$ | H | O | H | Cl | Cl | |
| 5-OC$_2$H$_5$ | H | H | O | H | Cl | Cl | |
| 5-CH$_3$ | H | H | O | H | CH$_3$OCH$_2$ | CH$_3$ | |
| 5-CH$_3$ | H | H | O | H | CH$_3$OCH$_2$ | Cl | |
| 4-CH(CH$_3$)$_2$ | H | H | O | H | CH$_3$ | OCH$_3$ | |
| H | H | H | O | H | SCH$_3$ | OCH$_3$ | |
| H | H | H | O | H | Br | OCH$_3$ | |
| H | H | O | O | H | —OCH(CH$_3$)$_2$ | OCH$_3$ | |
| H | H | | O | H | CF$_3$ | Cl | |
| H | H | | O | H | OC$_2$H$_5$ | Cl | |
| H | H | | S | H | CH$_3$ | CH$_3$ | |
| H | H | | S | H | CH$_3$ | OCH$_3$ | |
| H | H | | S | H | OCH$_3$ | OCH$_3$ | |
| H | H | H | O | CH$_3$ | CH$_3$ | CH$_3$ | |
| H | H | H | O | CH$_3$ | CH$_3$ | OCH$_3$ | |
| H | H | H | O | CH$_3$ | OCH$_3$ | OCH$_3$ | |
| H | H | H | O | OCH$_3$ | CH$_3$ | CH$_3$ | |
| H | H | H | O | OCH$_3$ | CH$_3$ | OCH$_3$ | |
| H | H | H | O | OCH$_3$ | OCH$_3$ | OCH$_3$ | |

TABLE II

| R | R$_1$ | R$_2$ | W | R$_8$ | X | Y | Z | m.p. (°C.) |
|---|---|---|---|---|---|---|---|---|
| H | H | H | O | H | CH$_2$ | CH$_3$ | CH | |
| H | H | H | O | H | CH$_3$ | OCH$_3$ | CH | |
| H | H | H | O | H | OCH$_3$ | OCH$_3$ | CH | |
| H | H | CH$_3$ | O | H | CH$_3$ | CH$_3$ | CH | |
| H | H | CH$_3$ | O | H | CH$_3$ | OCH$_3$ | CH | |
| H | H | CH$_3$ | O | H | OCH$_3$ | OCH$_3$ | CH | |
| H | CH$_3$ | CH$_3$ | O | H | CH$_3$ | CH$_3$ | CH | |
| H | CH$_3$ | CH$_3$ | O | H | CH$_3$ | OCH$_3$ | CH | |
| H | CH$_3$ | CH$_3$ | O | H | OCH$_3$ | OCH$_3$ | CH | |
| 5-F | H | H | O | H | CH$_3$ | CH$_3$ | CH | |
| 5-F | H | H | O | H | CH$_3$ | OCH$_3$ | CH | |
| 5-F | H | H | O | H | OCH$_3$ | OCH$_3$ | CH | |
| 5-Cl | H | H | O | H | CH$_3$ | CH$_3$ | CH | |
| 6-Cl | H | H | O | H | CH$_3$ | OCH$_3$ | CH | |
| 5-Cl | H | H | O | H | OCH$_3$ | OCH$_3$ | CH | |
| 5-NO$_2$ | H | H | O | H | CH$_3$ | CH$_3$ | CH | |
| 5-NO$_2$ | H | H | O | H | CH$_3$ | OCH$_3$ | CH | |
| 5-NO$_2$ | H | H | O | H | OCH$_3$ | OCH$_3$ | CH | |
| 5-OCH$_3$ | H | H | O | H | CH$_3$ | CH$_3$ | CH | |
| 4-OCH$_3$ | H | H | O | H | CH$_3$ | OCH$_3$ | CH | |
| 5-OCH$_3$ | H | H | O | H | OCH$_3$ | OCH$_3$ | CH | |
| 5-CF$_3$ | H | H | O | H | CH$_3$ | CH$_3$ | CH | |
| 5-CF$_3$ | H | H | O | H | CH$_3$ | OCH$_3$ | CH | |
| 3-CF$_3$ | H | H | O | H | OCH$_3$ | OCH$_3$ | CH | |
| H | H | H | O | H | H | CH$_3$ | CCl | |

TABLE II-continued

Structure: R-phenyl with C(R_1)(R_2)-OH substituent, SO_2NHC(=W)N(R_8)- linked to pyrimidine ring with X, Y, Z substituents.

| R | $R_1$ | $R_2$ | W | $R_8$ | X | Y | Z | m.p. (°C.) |
|---|---|---|---|---|---|---|---|---|
| H | H | H | O | H | $CH_3$ | $CH_3$ | C—CN | |
| H | H | H | O | H | $CH_3$ | $CH_3$ | C—$CH_3$ | |
| H | H | H | O | H | H | $CH_3$ | C—$CH_3$ | |
| H | H | H | O | H | $CH_3$ | $CH_3$ | C—$CH_2CH_3$ | |
| H | H | H | O | H | H | $CH_3$ | C—$CH_2CH_3$ | |
| H | H | H | O | H | H | $CH_3$ | C—$CH_2CH_2Cl$ | |
| H | H | H | O | H | $CH_3$ | $CH_3$ | C—$CH_2CH_2Cl$ | |
| H | H | H | O | H | $CH_3$ | $CH_3$ | C—$CH_2CH=CH_2$ | |
| H | H | H | O | H | H | $CH_3$ | C—$CH_2CH=CH_2$ | |
| 5-$OCH_2CH_2CH_3$ | H | H | O | H | $CH_3$ | $CH_3$ | CH | |
| 5-$CH_2CH_2CH_3$ | H | H | O | H | $CH_3$ | $OCH_3$ | CH | |
| H | $CH_3$ | H | O | H | H | $CH_3$ | C—$C_2H_5$ | |
| H | $CH_3$ | $CH_3$ | O | H | H | $OCH_3$ | C—Cl | |
| H | H | H | S | H | $CH_3$ | $CH_3$ | CH | |
| H | H | H | S | H | $CH_3$ | $OCH_3$ | CH | |
| H | H | H | S | H | $OCH_3$ | $OCH_3$ | CH | |
| H | H | H | O | $CH_3$ | $CH_3$ | $CH_3$ | CH | |
| H | H | H | O | $CH_3$ | $CH_3$ | $OCH_3$ | CH | |
| H | H | H | O | $CH_3$ | $OCH_3$ | $OCH_3$ | CH | |
| H | H | H | O | $OCH_3$ | $CH_3$ | $CH_3$ | CH | |
| H | H | H | O | $OCH_3$ | $CH_3$ | $OCH_3$ | CH | |
| H | H | H | O | $OCH_3$ | $OCH_3$ | $OCH_3$ | CH | |
| 5-$CH_3$ | H | H | O | H | $CH_3$ | $OCH_3$ | CH | |
| 4-$CH_3$ | H | H | O | H | $OCH_3$ | $OCH_3$ | CH | |
| H | H | H | O | H | Cl | Cl | CH | |
| H | $CH_3$ | H | O | H | Cl | Cl | CH | |
| 5-$OC_2H_5$ | H | H | O | H | Cl | Cl | CH | |
| 4-CH($CH_3$)$_2$ | H | H | O | H | —$CH_2OCH_3$ | $CH_3$ | CH | |
| H | H | H | O | H | —$CH_2OCH_3$ | $CH_3$ | CH | |
| H | H | H | O | H | $SCH_3$ | $OCH_3$ | CH | |
| H | H | H | O | H | $SCH_3$ | $CH_3$ | CH | |
| H | H | H | O | H | $SCH_3$ | Cl | CH | |
| H | H | H | O | H | $CF_3$ | Cl | CH | |
| H | H | H | O | H | —OCH($CH_3$)$_2$ | $OCH_3$ | CH | |
| H | H | $CH_3$ | O | H | $OC_2H_5$ | $OCH_3$ | CH | |
| H | H | H | O | H | $CF_3$ | $CH_3$ | CH | |

TABLE III

Structure: R-phenyl with C(R_1)(R_2)-OH substituent, SO_2NHC(=W)N(R_8)- linked to fused bicyclic pyrimidine ring with Y' and Q substituents.

| R | $R_1$ | $R_2$ | W | $R_8$ | Y' | Q | m.p. (°C.) |
|---|---|---|---|---|---|---|---|
| H | H | H | O | H | $CH_3$ | O | |
| H | H | H | O | H | $OCH_3$ | O | |
| H | H | $CH_3$ | O | H | $CH_3$ | O | |
| H | H | $CH_3$ | O | H | $OCH_3$ | O | |
| H | $CH_3$ | $CH_3$ | O | H | $CH_3$ | O | |
| H | $CH_3$ | $CH_3$ | O | H | $OCH_3$ | O | |
| 5-F | H | H | O | H | $OCH_3$ | O | |
| 5-Cl | H | H | O | H | $OCH_3$ | O | |
| 5-$CH_3$ | H | H | O | H | $OCH_3$ | O | |
| 5-$NO_2$ | H | H | O | H | $OCH_3$ | O | |
| 5-$OCH_3$ | H | H | O | H | $OCH_3$ | O | |
| 5-Cl | H | H | O | H | $CH_3$ | O | |
| H | H | H | O | H | H | $CH_2$ | |
| H | H | H | O | H | Cl | $CH_2$ | |

TABLE III-continued

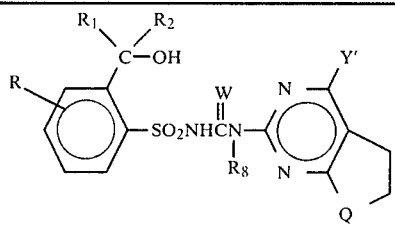

| R | R1 | R2 | W | R8 | Y' | Q | m.p. (°C.) |
|---|----|----|---|----|----|----|------------|
| H | H | H | O | H | CH3 | CH2 | |
| H | H | H | O | H | OCH3 | CH2 | |
| H | H | H | O | H | H | O | |
| 5-CH3 | H | H | O | H | OCH3 | O | |
| 4-CH(CH3)2 | H | H | O | H | OCH3 | O | |
| 5-OC2H5 | H | H | O | H | CH3 | O | |
| 4-CH3 | H | H | O | H | Cl | O | |
| 4-OCH2CH2CH3 | H | H | O | H | OCH3 | O | |
| H | H | H | S | H | CH3 | O | |
| H | H | H | S | H | CH3 | CH2 | |
| H | H | H | S | H | OCH3 | O | |
| H | H | H | S | H | OCH3 | CH2 | |
| H | H | H | O | CH3 | CH3 | O | |
| H | H | H | O | CH3 | CH3 | CH2 | |
| H | H | H | O | CH3 | OCH3 | O | |
| H | H | H | O | CH3 | OCH3 | CH2 | |
| H | H | H | O | H | OC2H5 | O | |
| H | H | H | O | H | OC2H5 | CH2 | |

TABLE IIIa

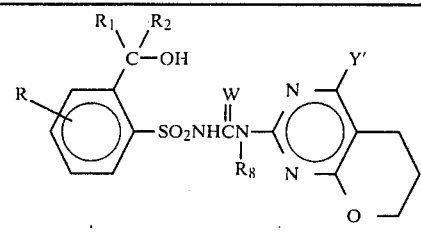

| R | R1 | R2 | W | R8 | Y' | m.p. (°C.) |
|---|----|----|---|----|----|------------|
| H | H | H | O | H | CH3 | |
| H | H | H | O | H | OCH3 | |
| H | H | CH3 | O | H | CH3 | |
| H | H | CH3 | O | H | OCH3 | |
| H | CH3 | CH3 | O | H | CH3 | |
| H | CH3 | CH3 | O | H | OCH3 | |
| 5-F | H | H | O | H | OCH3 | |
| 5-Cl | H | H | O | H | OCH3 | |
| 5-CH3 | H | H | O | H | OCH3 | |
| 5-NO2 | H | H | O | H | OCH3 | |
| 5-OCH3 | H | H | O | H | OCH3 | |
| 5-Cl | H | H | O | H | CH3 | |
| H | H | H | O | H | H | |
| H | H | H | O | H | Cl | |
| H | H | H | O | H | CH3 | |
| H | H | H | O | H | OCH3 | |
| H | H | H | O | H | H | |
| 5-CH3 | H | H | O | H | OCH3 | |
| 4-CH(CH3)2 | H | H | O | H | OCH3 | |
| 5-OC2H5 | H | H | O | H | CH3 | |
| 4-CH3 | H | H | O | H | Cl | |
| 4-OCH2CH2CH3 | H | H | O | H | OCH3 | |
| H | H | H | S | H | CH3 | |
| H | H | H | S | H | CH3 | |
| H | H | H | S | H | OCH3 | |
| H | H | H | S | H | OCH3 | |
| H | H | H | O | CH3 | CH3 | |
| H | H | H | O | CH3 | CH3 | |
| H | H | H | O | CH3 | OCH3 | |
| H | H | H | O | CH3 | OCH3 | |
| H | H | H | O | H | OC2H5 | |
| H | H | H | O | H | OC2H5 | |

TABLE IV

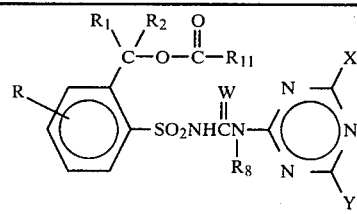

| R | R1 | R2 | R11 | W | R8 | X | Y | m.p.(°C.) |
|---|----|----|-----|---|----|----|----|-----------|
| H | H | H | H | O | H | CH3 | CH3 | |
| H | H | H | H | O | H | CH3 | OCH3 | |
| H | H | H | H | O | H | OCH3 | OCH3 | |
| H | H | H | —CH3 | O | H | CH3 | CH3 | |
| H | H | H | —CH3 | O | H | CH3 | OCH3 | |
| H | H | H | —CH3 | O | H | OCH3 | OCH3 | |
| H | H | H | —CH2CH3 | O | H | CH3 | OCH3 | |
| H | H | H | —CH2CH3 | O | H | OCH3 | OCH3 | |
| H | H | H | CF3 | O | H | OCH3 | OCH3 | |
| H | H | H | CF3 | O | H | CH3 | OCH3 | |
| H | H | H | CH2Cl | O | H | CH3 | OCH3 | |
| H | H | H | CH2CH=CH2 | O | H | CH3 | OCH3 | |
| H | H | H | –⟨phenyl⟩ | O | H | CH3 | OCH3 | |
| H | H | H | –⟨phenyl⟩ | O | H | OCH3 | OCH3 | |

TABLE IV-continued

Structure:

$$R_1, R_2 \text{ on } C-O-C(=O)-R_{11} \text{ attached to phenyl ring bearing } R \text{ and } SO_2NHC(=W)N(R_8)-\text{pyrimidine with } X, Y$$

| R | R$_1$ | R$_2$ | R$_{11}$ | W | R$_8$ | X | Y | m.p.(°C.) |
|---|---|---|---|---|---|---|---|---|
| H | H | H | 2,4-dichlorophenyl | O | H | CH$_3$ | OCH$_3$ | |
| H | H | H | 4-nitrophenyl | O | H | OCH$_3$ | OCH$_3$ | |
| H | H | CH$_3$ | CH$_3$ | O | H | OCH$_3$ | OCH$_3$ | |
| H | CH$_3$ | CH$_3$ | CH$_3$ | O | H | OCH$_3$ | OCH$_3$ | |
| 5-F | H | H | CH$_3$ | O | H | OCH$_3$ | OCH$_3$ | |
| 6-Cl | H | H | CH$_3$ | O | H | OCH$_3$ | OCH$_3$ | |
| 5-CH$_3$ | H | H | CH$_3$ | O | H | OCH$_3$ | OCH$_3$ | |
| 5-NO$_2$ | H | H | CH$_3$ | O | H | OCH$_3$ | OCH$_3$ | |
| 4-OCH$_3$ | H | H | CH$_3$ | O | H | OCH$_3$ | OCH$_3$ | |
| 5-CF$_3$ | H | H | CH$_3$ | O | H | OCH$_3$ | OCH$_3$ | |
| 3-Cl | H | H | CH$_3$ | O | H | CH$_3$ | OCH$_3$ | |
| 6-Cl | H | H | CH$_3$ | O | H | CH$_3$ | OCH$_3$ | |
| H | H | H | CH$_3$ | O | H | Cl | Cl | |
| H | H | H | CH$_3$ | O | H | Cl | OCH$_3$ | |
| H | H | H | CH$_3$ | O | H | Br | OCH$_3$ | |
| H | H | H | CH$_3$ | O | H | CH$_2$CH$_3$ | OCH$_3$ | |
| H | H | H | CH$_3$ | O | H | OCH$_2$CH$_3$ | CH$_3$ | |
| H | H | H | CH$_3$ | O | H | OCH(CH$_3$)$_2$ | CH$_3$ | |
| H | H | H | CH$_3$ | O | H | CF$_3$ | OCH$_3$ | |
| H | H | H | CH$_3$ | O | H | SCH$_3$ | OCH$_3$ | |
| H | H | H | CH$_3$ | O | H | CH$_2$OCH$_3$ | CH$_3$ | |
| H | H | H | CH$_3$ | O | H | CH$_2$OCH$_3$ | OCH$_3$ | |
| H | H | H | CH$_3$ | O | H | H | CH$_3$ | |
| H | H | H | CH$_3$ | O | H | H | OCH$_3$ | |
| H | H | H | phenyl | O | H | Cl | Cl | |
| H | H | H | phenyl | O | H | OCH$_3$ | OCH$_3$ | |
| H | H | H | —CH=CH$_2$ | O | H | CH$_3$ | OCH$_3$ | |
| H | H | H | —C≡CH | O | H | CH$_3$ | OCH$_3$ | |
| H | H | H | —C≡CCH$_3$ | O | H | OCH$_3$ | CH$_3$ | |
| H | H | H | (n-C$_5$H$_{11}$) | O | H | OCH$_3$ | CH$_3$ | |
| H | H | H | —CH$_2$OCH$_3$ | O | H | OCH$_3$ | CH$_3$ | |
| H | H | H | cyclopropyl | O | H | OCH$_3$ | OCH$_3$ | |
| H | H | H | cyclohexyl | O | H | OCH$_3$ | CH$_3$ | |
| H | H | H | CH$_3$ | O | H | SCH$_3$ | OCH$_3$ | |
| H | H | H | CH$_3$ | O | H | CF$_3$ | OCH$_3$ | |
| 5-CH(CH$_3$)$_2$ | H | H | CH$_3$ | O | H | OCH$_3$ | CH$_3$ | |
| 5-OC$_2$H$_5$ | H | H | CH$_3$ | O | H | OCH$_3$ | OCH$_3$ | |
| H | H | H | CH$_3$ | O | H | Br | OCH$_3$ | |
| H | H | H | —CH$_2$OCH$_3$ | O | H | SCH$_3$ | CH$_3$ | |
| H | H | H | cyclopropyl | O | H | SCH$_3$ | OCH$_3$ | |
| H | H | H | cyclohexyl | O | H | SCH$_3$ | CH$_3$ | |
| H | H | H | CH$_3$ | O | H | SCH$_3$ | CH$_3$ | |
| H | H | H | CH$_3$ | O | H | CF$_3$ | OCH$_3$ | |
| H | H | H | CH$_3$ | O | H | CH$_2$OCH$_3$ | OCH$_3$ | |
| H | H | H | 2-nitrophenyl | O | H | OCH$_3$ | CH$_3$ | |

TABLE IV-continued

Structure: R-phenyl with -C(R1)(R2)-O-C(=O)-R11 substituent and -SO2NH-C(=W)-N(R8)- linked to pyrimidine ring with X and Y substituents

| R | R1 | R2 | R11 | W | R8 | X | Y | m.p.(°C.) |
|---|----|----|-----|---|----|----|----|-----------|
| H | H | H | 2,4-dichlorophenyl | O | H | OCH3 | CH3 | |
| H | H | H | 2,4-dimethoxyphenyl | O | H | OCH3 | OCH3 | |
| H | H | H | CH3 | S | H | CH3 | CH3 | |
| H | H | H | CH3 | S | H | CH3 | OCH3 | |
| H | H | H | CH3 | S | H | OCH3 | OCH3 | |
| H | H | H | CH3 | O | CH3 | CH3 | CH3 | |
| H | H | H | CH3 | O | CH3 | CH3 | OCH3 | |
| H | H | H | CH3 | O | CH3 | OCH3 | OCH3 | |
| H | H | H | CH3 | O | OCH3 | CH3 | CH3 | |
| H | H | H | CH3 | O | OCH3 | CH3 | OCH3 | |
| H | H | H | CH3 | O | OCH3 | OCH3 | OCH3 | |

TABLE V

Structure: R-phenyl with -C(R1)(R2)-O-C(=O)-R11 substituent and -SO2NH-C(=W)-N(R8)- linked to triazine/pyrimidine ring with X, Y, Z substituents

| R | R1 | R2 | R11 | W | R8 | X | Y | Z | m.p.(°C.) |
|---|----|----|-----|---|----|----|----|---|-----------|
| H | H | H | H | O | H | CH3 | CH3 | CH | |
| H | H | H | H | O | H | CH3 | OCH3 | CH | |
| H | H | H | H | O | H | OCH3 | OCH3 | CH | |
| H | H | H | CH3 | O | H | CH3 | CH3 | CH | |
| H | H | H | CH3 | O | H | CH3 | OCH3 | CH | |
| H | H | H | CH3 | O | H | OCH3 | OCH3 | CH | |
| H | H | H | CH2CH3 | O | H | CH3 | OCH3 | CH | |
| H | H | H | CH2CH3 | O | H | OCH3 | OCH3 | CH | |
| H | H | H | CF3 | O | H | OCH3 | OCH3 | CH | |
| H | H | H | CF3 | O | H | CH3 | OCH3 | CH | |
| H | H | H | CH2Cl | O | H | CH3 | OCH3 | CH | |
| H | H | H | CH2CH=CH2 | O | H | CH3 | OCH3 | CH | |
| H | H | H | phenyl | O | H | CH3 | OCH3 | CH | |
| H | H | H | phenyl | O | H | OCH3 | OCH3 | CH | |
| H | H | H | 2,6-dichlorophenyl | O | H | CH3 | OCH3 | CH | |
| H | H | H | 4-nitrobenzyl-Cl | O | H | OCH3 | OCH3 | CH | |
| H | H | CH3 | CH3 | O | H | OCH3 | OCH3 | CH | |
| H | CH3 | CH3 | CH3 | O | H | OCH3 | OCH3 | CH | |
| 5-F | H | H | CH3 | O | H | OCH3 | OCH3 | CH | |
| 6-Cl | H | H | CH3 | O | H | OCH3 | OCH3 | CH | |

TABLE V-continued

Structure:
$$R_1, R_2, C-O-C(=O)-R_{11}$$ on a benzene ring with R substituent, $SO_2NHC(=W)N(R_8)$-pyrimidine with X, Y, Z substituents.

| R | R₁ | R₂ | R₁₁ | W | R₈ | X | Y | Z | m.p.(°C) |
|---|---|---|---|---|---|---|---|---|---|
| H | H | H | 2,4-dichlorophenyl | O | H | OCH₃ | OCH₃ | CH | |
| 5-CH₃ | H | H | CH₃ | O | H | OCH₃ | OCH₃ | CH | |
| 5-NO₂ | H | H | CH₃ | O | H | OCH₃ | OCH₃ | CH | |
| 5-OCH₃ | H | H | CH₃ | O | H | OCH₃ | OCH₃ | CH | |
| 5-CF₃ | H | H | CH₃ | O | H | OCH₃ | OCH₃ | CH | |
| 4-Cl | H | H | CH₃ | O | H | CH₃ | OCH₃ | CH | |
| 6-Cl | H | H | CH₃ | O | H | CH₃ | OCH₃ | CH | |
| H | H | H | CH₃ | O | H | Cl | Cl | CH | |
| H | H | H | CH₃ | O | H | Cl | OCH₃ | CH | |
| H | H | H | CH₃ | O | H | Br | OCH₃ | CH | |
| H | H | H | CH₃ | O | H | CH₂CH₃ | OCH₃ | CH | |
| H | H | H | CH₃ | O | H | OCH₂CH₃ | CH₃ | CH | |
| H | H | H | CH₃ | O | H | OCH(CH₃)₂ | CH₃ | CH | |
| H | H | H | CH₃ | O | H | CF₃ | OCH₃ | CH | |
| H | H | H | CH₃ | O | H | SCH₃ | OCH₃ | CH | |
| H | H | H | CH₃ | O | H | CH₂OCH₃ | CH₃ | CH | |
| H | H | H | CH₃ | O | H | CH₂OCH₃ | OCH₃ | CH | |
| H | H | H | CH₃ | O | H | H | CH₃ | CH | |
| H | H | H | CH₃ | O | H | H | OCH₃ | CH | |
| H | H | H | phenyl | O | H | Cl | Cl | CH | |
| H | H | H | phenyl | O | H | OCH₃ | OCH₃ | CH | |
| H | H | H | CH₃ | O | H | H | CH₃ | CCl | |
| H | H | H | CH₃ | O | H | CH₃ | CH₃ | C—CN | |
| H | H | H | CH₃ | O | H | CH₃ | CH₃ | CCH₃ | |
| H | H | H | CH₃ | O | H | H | CH₃ | CCH₃ | |
| H | H | H | CH₃ | O | H | CH₃ | CH₃ | CCH₂CH₃ | |
| H | H | H | CH₃ | O | H | H | CH₃ | CCH₂CH₃ | |
| H | H | H | CH₃ | O | H | Cl | Cl | C—CH₂CH₂Cl | |
| H | H | H | CH₃ | O | H | H | CH₃ | C—CH₂CH₂Cl | |
| H | H | H | CH₃ | O | H | CH₃ | CH₃ | C—CH₂CH₂Cl | |
| H | H | H | CH₃ | O | H | CH₃ | CH₃ | C—CH₂CH=CH₂ | |
| H | H | H | CH₃ | O | H | H | CH₃ | C—CH₂CH=CH₂ | |
| H | H | H | —CH=CH₂ | S | H | CH₃ | OCH₃ | CH | |
| H | H | H | —C≡CCH₃ | S | H | CH₃ | OCH₃ | CH | |
| H | H | H | —C≡CCH₃ | S | H | OCH₃ | CH₃ | CH | |
| H | H | H | —(n-C₅H₁₁) | S | H | OCH₃ | CH₃ | CH | |
| H | H | H | —CH₂OCH₃ | S | H | OCH₃ | CH₃ | CH | |
| H | H | H | cyclopropyl | S | H | OCH₃ | OCH₃ | CH | |
| H | H | H | cyclohexyl | S | H | OCH₃ | CH₃ | CH | |
| H | H | H | CH₃ | S | H | SCH₃ | OCH₃ | CH | |
| H | H | H | CH₃ | S | H | CF₃ | OCH₃ | CH | |
| 5-CH(CH₃)₂ | H | H | CH₃ | S | H | OCH₃ | CH₃ | CH | |
| 5-C₂H₅ | H | H | CH₃ | S | H | OCH₃ | OCH₃ | CH | |
| H | H | H | CH₃ | S | H | CH₂OCH₃ | CH₃ | CH | |
| H | H | H | 3-nitrophenyl | S | H | CH₃ | OCH₃ | CH | |
| H | H | H | 2,4-dinitrophenyl | S | H | OCH₃ | OCH₃ | CH | |

TABLE V-continued

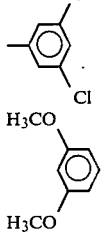

| R | R₁ | R₂ | R₁₁ | W | R₈ | X | Y | Z | m.p.(°C.) |
|---|----|----|-----|---|----|----|---|---|-----------|
| H | H | H | 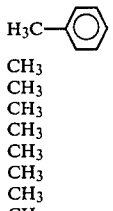 (2,5-dichlorophenyl) | S | H | CH₃ | OCH₃ | CH | |
| H | H | H | 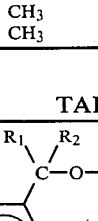 (3,5-dimethoxyphenyl) | S | H | CH₃ | OCH₃ | CH | |
| H | H | H |  (o-tolyl) | S | H | CH₃ | OCH₃ | CH | |
| H | H | H | CH₃ | S | H | CH₃ | CH₃ | CH | |
| H | H | H | CH₃ | S | H | CH₃ | OCH₃ | CH | |
| H | H | H | CH₃ | S | H | OCH₃ | OCH₃ | CH | |
| H | H | H | CH₃ | O | CH | CH₃ | CH₃ | CH | |
| H | H | H | CH₃ | O | CH | CH₃ | OCH₃ | CH | |
| H | H | H | CH₃ | O | CH | OCH₃ | OCH₃ | CH | |
| H | H | H | CH₃ | O | OCH | CH₃ | CH₃ | CH | |
| H | H | H | CH₃ | O | OCH | CH₃ | OCH₃ | CH | |
| H | H | H | CH₃ | O | OCH | OCH₃ | OCH₃ | CH | |

TABLE VI

| R | R₁ | R₂ | R₁₁ | W | R₈ | Y' | Q | m.p.(°C.) |
|---|----|----|-----|---|----|----|----|-----------|
| H | H | H | H | O | H | CH₃ | O | |
| H | H | H | H | O | H | OCH₃ | O | |
| H | H | H | CH₃ | O | H | CH₃ | O | |
| H | H | H | CH₃ | O | H | OCH₃ | O | |
| H | H | H | CH₂CH₃ | O | H | CH₃ | O | |
| H | H | H | CF₃ | O | H | CH₃ | O | |
| H | H | H | CF₃ | O | H | OCH₃ | O | |
| H | H | H | CH₂Cl | O | H | OCH₃ | O | |
| H | H | H | CH₂CH=CH₂ | O | H | OCH₃ | O | |
| H | H | H | phenyl | O | H | CH₃ | O | |
| H | H | H | phenyl | O | H | OCH₃ | O | |
| H | H | H |  (2,5-dichlorophenyl) | O | H | OCH₃ | O | |
| H | H | CH₃ | CH₃ | O | H | OCH₃ | O | |
| H | CH₃ | CH₃ | CH₃ | O | H | OCH₃ | O | |
| 5-F | H | H | CH₃ | O | H | OCH₃ | O | |
| 5-Cl | H | H | CH₃ | O | H | OCH₃ | O | |
| 5-CH₃ | H | H | CH₃ | O | H | OCH₃ | O | |
| 5-NO₂ | H | H | CH₃ | O | H | OCH₃ | O | |
| 5-OCH₃ | H | H | CH₃ | O | H | OCH₃ | O | |
| 3-CF₃ | H | H | CH₃ | O | H | OCH₃ | O | |
| 5-Cl | H | H | CH₃ | O | H | CH₃ | O | |
| 6-Cl | H | H | CH₃ | O | H | CH₃ | O | |

TABLE VI-continued

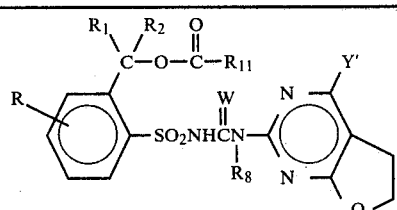

| R | R1 | R2 | R11 | W | R8 | Y' | Q | m.p.(°C.) |
|---|---|---|---|---|---|---|---|---|
| H | H | H | CH3 | O | H | H | O | |
| H | H | H | CH3 | O | H | H | CH2 | |
| H | H | H | CH3 | O | H | Cl | CH2 | |
| H | H | H | CH3 | O | H | CH3 | CH2 | |
| H | H | H | CH3 | O | H | OCH3 | CH2 | |
| H | H | H | CH3 | S | H | CH3 | O | |
| H | H | H | CH3 | S | H | OCH3 | CH2 | |
| H | H | H | CH3 | S | H | CH3 | O | |
| H | H | H | CH3 | S | H | OCH3 | CH2 | |
| H | H | H | CH3 | O | CH3 | CH3 | O | |
| H | H | H | CH3 | O | OCH3 | CH3 | CH2 | |
| H | H | H | CH3 | O | CH3 | OCH3 | O | |
| H | H | H | CH | O | OCH3 | OCH3 | CH2 | |
| H | H | H | CH | O | H | OC2H5 | O | |
| H | H | H | CH | O | H | OC2H5 | CH2 | |
| H | H | H | CH2OCH3 | O | H | CH3 | O | |
| H | H | H | ◁ | O | H | CH3 | O | |
| H | H | H | —CH=CH2 | O | H | CH3 | O | |
| H | H | H | C≡CH | O | H | CH3 | O | |
| H | H | H | —(n-C5H11) | O | H | CH3 | O | |
| 5-CH3 | H | H | cyclohexyl | O | H | CH3 | O | |
| 4-OC2H5 | H | H | —CH=CH2 | O | H | CH3 | O | |
| 4-CH3 | H | H | CH3 | O | H | CH3 | CH2 | |
| H | H | H | 3-NO2-phenyl | O | H | CH3 | O | |
| H | H | H | 2,4-dinitrophenyl | O | H | CH3 | O | |
| H | H | H | 3,5-dichlorophenyl | O | H | CH3 | O | |
| H | H | H | 3,4,5-trimethoxyphenyl | O | H | CH3 | O | |
| H | H | H | 4-methylphenyl | O | H | CH3 | O | |
| H | H | H | —CH2CHBr—CH2Br | O | H | OCH3 | O | |
| H | H | H | —CH2CHCl—CH2Cl | O | H | CH3 | O | |
| H | H | H | —CHCl2 | O | H | OCH3 | O | |
| H | H | H | CCl3 | O | H | OCH3 | O | |
| H | H | H | CHBr2 | O | H | OCH3 | O | |
| H | H | H | CH2Cl—CH=CH— | O | H | OCH3 | O | |
| H | H | H | —CH2—CHCl—CH2Cl | O | H | OCH3 | O | |

TABLE VIa

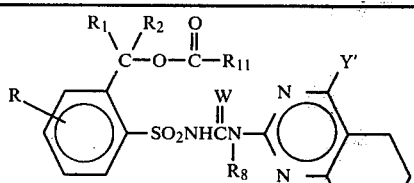

| R | R₁ | R₂ | R₁₁ | W | R₈ | Y' | m.p.(°C.) |
|---|----|----|-----|---|----|----|-----------|
| H | H | H | H | O | H | CH₃ | |
| H | H | H | H | O | H | OCH₃ | |
| H | H | H | CH₃ | O | H | CH₃ | |
| H | H | H | CH₃ | O | H | OCH₃ | |
| H | H | H | CH₂CH₃ | O | H | CH₃ | |
| H | H | H | CF₃ | O | H | CH₃ | |
| H | H | H | CF₃ | O | H | OCH₃ | |
| H | H | H | CH₂Cl | O | H | OCH₃ | |
| H | H | H | CH₂CH=CH₂ | O | H | OCH₃ | |
| H | H | H | —C₆H₅ | O | H | CH₃ | |
| H | H | H | —(2-CH₃-C₆H₄) | O | H | OCH₃ | |
| H | H | H | —(2-Cl-C₆H₄) | O | H | OCH₃ | |
| H | H | H | —(2,4-Cl₂-C₆H₃) | | | | |
| H | H | CH₃ | CH₃ | O | H | OCH₃ | |
| H | CH₃ | CH₃ | CH₃ | O | H | OCH₃ | |
| 5-F | H | H | CH₃ | O | H | OCH₃ | |
| 5-Cl | H | H | CH₃ | O | H | OCH₃ | |
| H | H | H | CH₂OCH₃ | O | H | CH₃ | |
| H | H | H | —cyclopropyl | O | H | CH₃ | |
| H | H | H | —CH=CH₂ | O | H | CH₃ | |
| H | H | H | —C≡CH | O | H | CH₃ | |
| H | H | H | —(n-C₅H₁₁) | O | H | CH₃ | |
| 5-CH₃ | H | H | —cyclohexyl | O | H | CH₃ | |
| 4-OC₂H₅ | H | H | —CH=CH₂ | O | H | CH₃ | |
| 4-CH₃ | H | H | CH₃ | O | H | CH₃ | |
| H | H | H | —(3-NO₂-C₆H₄) | O | H | CH₃ | |
| H | H | H | —(2-CH₃-3,5-(NO₂)₂-C₆H₂) | O | H | CH₃ | |
| H | H | H | —(3,5-Cl₂-C₆H₃) | O | H | CH₃ | |
| H | H | H | —(3,5-(OCH₃)₂-C₆H₃) | O | H | CH₃ | |
| H | H | H | —(4-CH₃-C₆H₄) | O | H | CH₃ | |
| H | H | H | —CH₂CHBr—CH₂Br | O | H | OCH₃ | |
| H | H | H | CH₂CF₃ | O | H | OCH₃ | |
| H | H | H | —CH₂CHCl—CH₂Cl | O | H | CH₃ | |
| H | H | H | —CHCl₂ | O | H | OCH₃ | |
| H | H | H | CCl₃ | O | H | OCH₃ | |
| H | H | H | CHBr₂ | O | H | OCH₃ | |

TABLE VIa-continued

| R | $R_1$ | $R_2$ | $R_{11}$ | W | $R_8$ | Y' | m.p.(°C.) |
|---|---|---|---|---|---|---|---|
| H | H | H | $CH_2Cl$ | O | H | $OCH_3$ | |
| H | H | H | $-CH_2-CH=CH$ | O | H | $OCH_3$ | |
| H | H | H | $-CH_2-CHCl-CH_2Cl$ | O | H | $OCH_3$ | |
| 5-$CH_3$ | H | H | $CH_3$ | O | H | $OCH_3$ | |
| 5-$NO_2$ | H | H | $CH_3$ | O | H | $OCH_3$ | |
| 5-$OCH_3$ | H | H | $CH_3$ | O | H | $OCH_3$ | |
| 3-$CF_3$ | H | H | $CH_3$ | O | H | $OCH_3$ | |
| 5-Cl | H | H | $CH_3$ | O | H | $CH_3$ | |
| 6-Cl | H | H | $CH_3$ | O | H | $CH_3$ | |
| H | H | H | $CH_3$ | O | H | H | |
| H | H | H | $CH_3$ | O | H | H | |
| H | H | H | $CH_3$ | O | H | Cl | |
| H | H | H | $CH_3$ | O | H | $CH_3$ | |
| H | H | H | $CH_3$ | O | H | $OCH_3$ | |
| H | H | H | $CH_3$ | S | H | $CH_3$ | |
| H | H | H | $CH_3$ | S | H | $OCH_3$ | |
| H | H | H | $CH_3$ | S | H | $CH_3$ | |
| H | H | H | $CH_3$ | S | H | $OCH_3$ | |
| H | H | H | $CH_3$ | O | $CH_3$ | $CH_3$ | |
| H | H | H | $CH_3$ | O | $OCH_3$ | $CH_3$ | |
| H | H | H | $CH_3$ | O | $CH_3$ | | |
| H | H | H | $CH_3$ | O | $OCH_3$ | $OCH_3$ | |
| H | H | H | $CH_3$ | O | H | $OC_2H_5$ | |
| H | H | H | $CH_3$ | O | H | $OC_2H_5$ | |

TABLE VII

| R | $R_1$ | $R_2$ | $R_{12}$ | W | $R_8$ | X | Y | m.p. (°C.) |
|---|---|---|---|---|---|---|---|---|
| H | H | H | H | O | H | $CH_3$ | $CH_3$ | |
| H | H | H | H | O | H | $CH_3$ | $OCH_3$ | |
| H | H | H | H | O | H | $OCH_3$ | $OCH_3$ | |
| H | H | H | $-CH_3$ | O | H | $CH_3$ | $CH_3$ | |
| H | H | H | $-CH_3$ | O | H | $CH_3$ | $OCH_3$ | |
| H | H | H | $-CH_3$ | O | H | $OCH_3$ | $OCH_3$ | |
| H | H | H | $-CH_2CH_3$ | O | H | $CH_3$ | $OCH_3$ | |
| H | H | H | $-CH_2CH_3$ | O | H | $OCH_3$ | $OCH_3$ | |
| H | H | H | $CH(CH_3)_2$ | O | H | $OCH_3$ | $OCH_3$ | |
| H | H | H | $CH(CH_3)_2$ | O | H | $CH_3$ | $OCH_3$ | |
| H | H | H | cyclohexyl | O | H | $CH_3$ | $OCH_3$ | |
| H | H | H | $CH_2CH=CH_2$ | O | H | $CH_3$ | $OCH_3$ | |
| H | H | H | phenyl | O | H | $CH_3$ | $OCH_3$ | |
| H | H | H | phenyl | O | H | $OCH_3$ | $OCH_3$ | |
| H | H | H | $CH_2$-(4-methylphenyl) | O | H | $CH_3$ | $OCH_3$ | |
| H | H | H | 4-$NO_2$-phenyl | O | H | $OCH_3$ | $OCH_3$ | |

TABLE VII-continued

| R | R₁ | R₂ | R₁₂ | W | R₈ | X | Y | m.p. (°C.) |
|---|---|---|---|---|---|---|---|---|
| H | H | CH₃ | CH₃ | O | H | OCH₃ | OCH₃ | |
| H | CH₃ | CH₃ | CH₃ | O | H | OCH₃ | OCH₃ | |
| 5-F | H | H | CH₃ | O | H | OCH₃ | OCH₃ | |
| 4-Cl | H | H | CH₃ | O | H | OCH₃ | OCH₃ | |
| 5-CH₃ | H | H | CH₃ | O | H | OCH₃ | OCH₃ | |
| 3-NO₂ | H | H | CH₃ | O | H | OCH₃ | OCH₃ | |
| 5-OCH₃ | H | H | CH₃ | O | H | OCH₃ | OCH₃ | |
| 5-CF₃ | H | H | CH₃ | O | H | OCH₃ | OCH₃ | |
| 5-Cl | H | H | CH₃ | O | H | CH₃ | OCH₃ | |
| 6-Cl | H | H | CH₃ | O | H | CH₃ | OCH₃ | |
| H | H | H | CH₃ | O | H | Cl | Cl | |
| H | H | H | CH₃ | O | H | Cl | OCH₃ | |
| H | H | H | CH₃ | O | H | Br | OCH₃ | |
| H | H | H | CH₃ | O | H | CH₂CH₃ | OCH₃ | |
| H | H | H | CH₃ | O | H | OCH₂CH₃ | CH₃ | |
| H | H | H | CH₃ | O | H | OCH(CH₃)₂ | CH₃ | |
| H | H | H | CH₃ | O | H | CF₃ | OCH₃ | |
| H | H | H | CH₃ | O | H | SCH₃ | OCH₃ | |
| H | H | H | CH₃ | O | H | CH₂OCH₃ | CH₃ | |
| H | H | H | CH₃ | O | H | CH₂OCH₃ | OCH₃ | |
| H | H | H | CH₃ | O | H | H | CH₃ | |
| H | H | H | CH₃ | O | H | H | OCH₃ | |
| H | H | H |  | O | H | Cl | Cl | |
| H | H | H |  | O | H | OCH₃ | OCH₃ | |
| H | H | H | CH₂—(CH₂)₄CH₃ | O | H | CH₃ | OCH₃ | |
| H | H | H | —CH₂—CH=CH—CH₃ | O | H | CH₃ | OCH₃ | |
| H | H | H |  | O | H | OCH₃ | OCH₃ | |
| H | H | H |  | O | H | OCH₃ | CH₃ | |
| H | H | H |  | O | H | OCH₃ | OCH₃ | |
| H | H | H |  | O | H | OCH₃ | CH₃ | |
| H | H | H |  | O | H | OCH₃ | CH₃ | |
| H | H | H |  | O | H | CH₃ | OCH₃ | |
| H | H | H |  | O | H | CH₃ | OCH₃ | |
| H | H | H |  | O | H | CH₃ | OCH₃ | |
| H | H | H |  | O | H | OCH₃ | OCH₃ | |

TABLE VII-continued

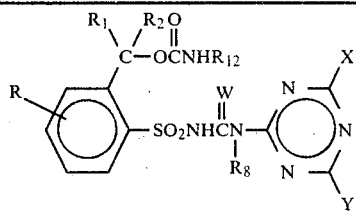

| R | R₁ | R₂ | R₁₂ | W | R₈ | X | Y | m.p. (°C.) |
|---|----|----|-----|---|----|---|---|-----------|
| H | H | H | H₂C—⟨phenyl⟩ | O | H | OCH₃ | OCH₃ | |
| H | H | H | —H₂C—⟨C₆H₄⟩—CH₃ | O | H | OCH₃ | CH₃ | |
| H | H | H | H₂C—⟨C₆H₄⟩—CH(CH₃)₂ | O | H | CH₃ | OCH₃ | |
| 5-OC₂H₅ | H | H | CH₃ | O | H | OCH₃ | OCH₃ | |
| 6-CH(CH₃)₂ | H | H | CH₃ | O | H | OCH₃ | OCH₃ | |
| 3-CF₃ | H | H | CH₃ | O | H | OCH₃ | OCH₃ | |
| H | H | H | CH₃ | S | H | CH₃ | CH₃ | |
| H | H | H | CH₃ | S | H | CH₃ | OCH₃ | |
| H | H | H | CH₃ | S | H | OCH₃ | OCH₃ | |
| H | H | H | CH₃ | O | CH₃ | CH₃ | CH₃ | |
| H | H | H | CH₃ | O | CH₃ | CH₃ | OCH₃ | |
| H | H | H | CH₃ | O | CH₃ | OCH₃ | OCH₃ | |
| H | H | H | CH₃ | O | OCH₃ | CH₃ | CH₃ | |
| H | H | H | CH₃ | O | OCH₃ | CH₃ | OCH₃ | |
| H | H | H | CH₃ | O | OCH₃ | OCH₃ | OCH₃ | |

TABLE VIII

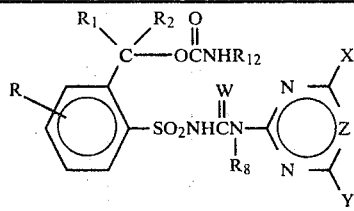

| R | R₁ | R₂ | R₁₂ | W | R₈ | X | Y | Z | m.p. (°C.) |
|---|----|----|-----|---|----|---|---|---|-----------|
| H | H | H | H | O | H | CH₃ | CH₃ | CH | |
| H | H | H | H | O | H | CH₃ | OCH₃ | CH | |
| H | H | H | H | O | H | OCH₃ | OCH₃ | CH | |
| H | H | H | —CH₃ | O | H | CH₃ | CH₃ | CH | |
| H | H | H | —CH₃ | O | H | CH₃ | OCH₃ | CH | |
| H | H | H | —CH₃ | O | H | OCH₃ | OCH₃ | CH | |
| H | H | H | —CH₂CH₃ | O | H | CH₃ | OCH₃ | CH | |
| H | H | H | —CH₂CH₃ | O | H | OCH₃ | OCH₃ | CH | |
| H | H | H | —CH(CH₃)₂ | O | H | OCH₃ | OCH₃ | CH | |
| H | H | H | —CH(CH₃)₂ | O | H | CH₃ | OCH₃ | CH | |
| H | H | H | ⟨cyclopentyl⟩ | O | H | CH₃ | OCH₃ | CH | |
| H | H | H | CH₂CH=CH₂ | O | H | CH₃ | OCH₃ | CH | |
| H | H | H | —⟨phenyl⟩ | O | H | OCH₃ | OCH₃ | CH | |
| H | H | H | —CH₂—⟨phenyl⟩ | O | H | CH₃ | OCH₃ | CH | |
| H | H | H | —⟨C₆H₄⟩—NO₂ | O | H | OCH₃ | OCH₃ | CH | |
| H | H | CH₃ | CH₃ | O | H | OCH₃ | OCH₃ | CH | |
| H | CH₃ | CH₃ | CH₃ | O | H | OCH₃ | OCH₃ | CH | |

TABLE VIII-continued

| R | R₁ | R₂ | R₁₂ | W | R₈ | X | Y | Z | m.p. (°C.) |
|---|----|----|-----|---|----|---|---|---|------------|
| 5-F | H | H | $CH_3$ | O | H | $OCH_3$ | $OCH_3$ | CH | |
| 5-Cl | H | H | $CH_3$ | O | H | $OCH_3$ | $OCH_3$ | CH | |
| H | H | H | $CH_2$—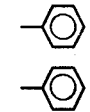 | O | H | $OCH_3$ | $OCH_3$ | CH | |
| 5-$CH_3$ | H | H | $CH_3$ | O | H | $OCH_3$ | $OCH_3$ | CH | |
| 5-$NO_2$ | H | H | $CH_3$ | O | H | $OCH_3$ | $OCH_3$ | CH | |
| 5-$OCH_3$ | H | H | $CH_3$ | O | H | $OCH_3$ | $OCH_3$ | CH | |
| 4-$CF_3$ | H | H | $CH_3$ | O | H | $OCH_3$ | $OCH_3$ | CH | |
| 5-Cl | H | H | $CH_3$ | O | H | $CH_3$ | $OCH_3$ | CH | |
| 6-Cl | H | H | $CH_3$ | O | H | $CH_3$ | $OCH_3$ | CH | |
| H | H | H | $CH_3$ | O | H | Cl | Cl | CH | |
| H | H | H | $CH_3$ | O | H | Cl | $OCH_3$ | CH | |
| H | H | H | $CH_3$ | O | H | Br | $OCH_3$ | CH | |
| H | H | H | $CH_3$ | O | H | $CH_2CH_3$ | $OCH_3$ | CH | |
| H | H | H | $CH_3$ | O | H | $OCH_2CH_3$ | $CH_3$ | CH | |
| H | H | H | $CH_3$ | O | H | $OCH(CH_3)_2$ | $CH_3$ | CH | |
| H | H | H | $CH_3$ | O | H | $CF_3$ | $OCH_3$ | CH | |
| H | H | H | $CH_3$ | O | H | $SCH_3$ | $OCH_3$ | CH | |
| H | H | H | $CH_3$ | O | H | $CH_2OCH_3$ | $CH_3$ | CH | |
| H | H | H | $CH_3$ | O | H | $CH_2OCH_3$ | $OCH_3$ | CH | |
| H | H | H | $CH_3$ | O | H | H | $CH_3$ | CH | |
| H | H | H | $CH_3$ | O | H | H | $OCH_3$ | CH | |
| H | H | H |  | O | H | Cl | Cl | CH | |
| H | H | H |  | O | H | $OCH_3$ | $OCH_3$ | CH | |
| H | H | H | $CH_3$ | O | H | H | $CH_3$ | CCl | |
| H | H | H | $CH_3$ | O | H | $CH_3$ | $CH_3$ | C—CN | |
| H | H | H | $CH_3$ | O | H | $CH_3$ | $CH_3$ | $CCH_3$ | |
| H | H | H | $CH_3$ | O | H | H | $CH_3$ | $CCH_3$ | |
| H | H | H | $CH_3$ | O | H | $CH_3$ | $CH_3$ | $CCH_2CH_3$ | |
| H | H | H | $CH_3$ | O | H | H | $CH_3$ | $CCH_2CH_3$ | |
| H | H | H | $CH_3$ | O | H | Cl | Cl | C—$CH_2CH_2Cl$ | |
| H | H | H | $CH_3$ | O | H | H | $CH_3$ | C—$CH_2CH_2Cl$ | |
| H | H | H | $CH_3$ | O | H | $CH_3$ | $CH_3$ | C—$CH_2CH_2Cl$ | |
| H | H | H | $CH_3$ | O | H | $CH_3$ | $CH_3$ | C—$CH_2CH=CH_2$ | |
| H | H | H | $CH_3$ | O | H | H | $CH_3$ | C—$CH_2CH=CH_2$ | |
| H | H | H | $CH_2$—$(CH_2)_4CH_3$ | O | H | $CH_3$ | $OCH_3$ | CH | |
| H | H | H | —$CH_2$—CH=CH—$CH_3$ | O | H | $CH_3$ | $OCH_3$ | CH | |
| H | H | H |  | O | H | $OCH_3$ | $OCH_3$ | CH | |
| H | H | H |  | O | H | $OCH_3$ | $OCH_3$ | CH | |
| H | H | H |  | O | H | $OCH_3$ | $CH_3$ | CH | |
| H | H | H |  | O | H | $OCH_3$ | $CH_3$ | CH | |
| H | H | H |  | O | H | $OCH_3$ | $CH_3$ | CH | |
| H | H | H |  | O | H | $CH_3$ | $OCH_3$ | CH | |
| H | H | H |  | O | H | $CH_3$ | $OCH_3$ | CH | |
| H | H | H |  | O | H | $OCH_3$ | $OCH_3$ | CH | |

TABLE VIII-continued

| R | R₁ | R₂ | R₁₂ | W | R₈ | X | Y | Z | m.p. (°C.) |
|---|----|----|-----|---|----|----|----|----|----|
| H | H | H | -⟨C₆H₄⟩-CF₃ (4-) | O | H | CH₃ | OCH₃ | CH | |
| H | H | H | -⟨C₆H₄⟩-Cl (4-) | O | H | OCH₃ | OCH₃ | CH | |
| H | H | H | H₂C-⟨C₆H₄⟩-CH(CH₃)₂ | O | H | OCH₃ | CH₃ | CH | |
| 5-OC₂H₅ | H | H | CH₃ | O | H | OCH₃ | CH₃ | CH | |
| 6-CH(CH₃)₂ | H | H | CH₃ | O | H | OCH₃ | CH₃ | CH | |
| 4-C₂H₅ | H | H | CH₃ | O | H | OCH₃ | OCH₃ | CH | |
| 5-CH₃ | CH₃ | H | CH₃ | O | H | OCH₃ | OCH₃ | CH | |
| H | H | H | CH₃ | S | H | CH₃ | CH₃ | CH | |
| H | H | H | CH₃ | S | H | CH₃ | OCH₃ | CH | |
| H | H | H | CH₃ | S | H | OCH₃ | OCH₃ | CH | |
| H | H | H | CH₃ | O | CH₃ | CH₃ | CH₃ | CH | |
| H | H | H | CH₃ | O | CH₃ | CH₃ | OCH₃ | CH | |
| H | H | H | CH₃ | O | CH₃ | OCH₃ | OCH₃ | CH | |
| H | H | H | CH₃ | O | OCH₃ | CH₃ | CH₃ | CH | |
| H | H | H | CH₃ | O | OCH₃ | CH₃ | OCH₃ | CH | |
| H | H | H | CH₃ | O | OCH₃ | OCH₃ | OCH₃ | CH | |

TABLE IX

| R | R₁ | R₂ | R₁₂ | W | R₈ | Y' | Q | m.p. (°C.) |
|---|----|----|-----|---|----|----|---|----|
| H | H | H | H | O | H | CH₃ | O | |
| H | H | H | H | O | H | OCH₃ | O | |
| H | H | H | —CH₃ | O | H | CH₃ | O | |
| H | H | H | —CH₃ | O | H | OCH₃ | O | |
| H | H | H | —CH₂CH₃ | O | H | CH₃ | O | |
| H | H | H | —CH(CH₃)₂ | O | H | CH₃ | O | |
| H | H | H | —CH(CH₃)₂ | O | H | OCH₃ | O | |
| H | H | H | -⟨cyclohexyl⟩ | O | H | OCH₃ | O | |
| H | H | H | CH₂CH=CH₂ | O | H | OCH₃ | O | |
| H | H | H | -⟨C₆H₅⟩ | O | H | CH₃ | O | |
| H | H | H | -⟨C₆H₅⟩ | O | H | OCH₃ | O | |
| H | H | H | CH₂-⟨C₆H₅⟩ | O | H | OCH₃ | O | |
| H | H | CH₃ | CH₃ | O | H | OCH₃ | O | |
| H | CH₃ | CH₃ | CH₃ | O | H | OCH₃ | O | |
| 3-F | H | H | CH₃ | O | H | OCH₃ | O | |
| 5-Cl | H | H | CH₃ | O | H | OCH₃ | O | |
| 5-CH₃ | H | H | CH₃ | O | H | OCH₃ | O | |
| 5-NO₂ | H | H | CH₃ | O | H | OCH₃ | O | |
| 4-OCH₃ | H | H | CH₃ | O | H | OCH₃ | O | |
| 5-CF₃ | H | H | CH₃ | O | H | OCH₃ | O | |

TABLE IX-continued

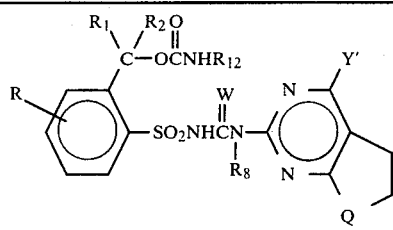

| R | R₁ | R₂ | R₁₂ | W | R₈ | Y' | Q | m.p. (°C.) |
|---|---|---|---|---|---|---|---|---|
| 5-Cl | H | H | CH₃ | O | H | CH₃ | O | |
| 6-Cl | H | H | CH₃ | O | H | CH₃ | O | |
| H | H | H | CH₃ | O | H | H | O | |
| H | H | H | CH₃ | O | H | H | CH₂ | |
| H | H | H | CH₃ | O | H | Cl | CH₂ | |
| H | H | H | CH₃ | O | H | CH₃ | CH₂ | |
| H | H | H | CH₃ | O | H | OCH₃ | CH₂ | |
| H | H | H | CH₃ | S | H | CH₃ | CH₂ | |
| H | H | H | CH₃ | S | H | OCH₃ | O | |
| H | H | H | CH₃ | S | H | CH₃ | CH₂ | |
| H | H | H | CH₃ | S | H | OCH₃ | O | |
| H | H | H | CH₃ | O | CH₃ | CH₃ | O | |
| H | H | H | CH₃ | O | CH₃ | CH₃ | CH₂ | |
| H | H | H | CH₃ | O | CH₃ | OCH₃ | O | |
| H | H | H | CH₃ | O | CH₃ | OCH₃ | CH₂ | |
| H | H | H | CH₃ | O | OCH₃ | CH₃ | O | |
| H | H | H | CH₃ | O | OCH₃ | CH₃ | CH₂ | |
| H | H | H | CH₃ | O | OCH₃ | OCH₃ | O | |
| H | H | H | CH₃ | O | OCH₃ | OCH₃ | CH₂ | |
| H | H | H | CH₃ | O | H | OC₂H₅ | O | |
| H | H | H | CH₃ | O | H | OC₂H₅ | CH₂ | |
| H | H | H | —CH₂—(CH₂)₄CH₃ | O | H | OCH₃ | O | |
| H | H | H | CH₂—CH=CH—CH₃ | O | H | CH₃ | O | |
| H | H | H |  | O | H | OCH₃ | O | |
| H | H | H |  | O | H | OCH₃ | O | |
| H | H | H |  | O | H | OCH₃ | O | |
| H | H | H | 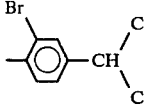 | O | H | OCH₃ | O | |
| H | H | H | 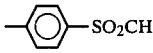 | O | H | OCH₃ | O | |
| H | H | H | 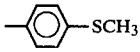 | O | H | CH₃ | O | |
| H | H | H |  | O | H | Cl | O | |
| H | H | H |  | O | H | Cl | O | |
| H | H | H | 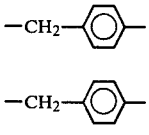 | O | H | OCH₃ | O | |
| 5-OC₂H₅ | H | H | CH₃ | O | H | OCH₃ | O | |
| 4-CH(CH₃)₂ | H | H | CH₃ | O | H | OCH₃ | O | |
| 5-CF₃ | H | H | 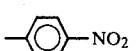 | O | H | OCH₃ | O | |

TABLE IXa

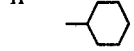

| R | R₁ | R₂ | R₁₂ | W | R₈ | Y' | m.p. (°C.) |
|---|----|----|-----|---|----|----|------------|
| H | H | H | H | O | H | $CH_3$ | |
| H | H | H | H | O | H | $OCH_3$ | |
| H | H | H | $-CH_3$ | O | H | $CH_3$ | |
| H | H | H | $-CH_3$ | O | H | $OCH_3$ | |
| H | H | H | $-CH_2CH_3$ | O | H | $CH_3$ | |
| H | H | H | $-CH(CH_3)_2$ | O | H | $CH_3$ | |
| H | H | H | $-CH(CH_3)_2$ | O | H | $OCH_3$ | |
| H | H | H | cyclohexyl | O | H | $OCH_3$ | |
| H | H | H | $CH_2CH=CH_2$ | O | H | $OCH_3$ | |
| H | H | H | phenyl | O | H | $CH_3$ | |
| H | H | H | phenyl | O | H | $OCH_3$ | |
| H | H | H | $CH_2$-phenyl | O | H | $OCH_3$ | |
| H | H | $CH_3$ | $CH_3$ | O | H | $OCH_3$ | |
| H | $CH_3$ | $CH_3$ | $CH_3$ | O | H | $OCH_3$ | |
| 3-F | H | H | $CH_3$ | O | H | $OCH_3$ | |
| 5-Cl | H | H | $CH_3$ | O | H | $OCH_3$ | |
| 5-$CH_3$ | H | H | $CH_3$ | O | H | $OCH_3$ | |
| 5-$NO_2$ | H | H | $CH_3$ | O | H | $OCH_3$ | |
| 4-$OCH_3$ | H | H | $CH_3$ | O | H | $OCH_3$ | |
| 5-$CF_3$ | H | H | $CH_3$ | O | H | $OCH_3$ | |
| 5-Cl | H | H | $CH_3$ | O | H | $CH_3$ | |
| 6-Cl | H | H | $CH_3$ | O | H | $CH_3$ | |
| H | H | H | $CH_3$ | O | H | H | |
| H | H | H | $CH_3$ | O | H | H | |
| H | H | H | $CH_3$ | O | H | Cl | |
| H | H | H | $CH_3$ | O | H | $CH_3$ | |
| H | H | H | $CH_3$ | O | H | $OCH_3$ | |
| H | H | H | $CH_3$ | S | H | $CH_3$ | |
| H | H | H | $CH_3$ | S | H | $OCH_3$ | |
| H | H | H | $CH_3$ | S | H | $CH_3$ | |
| H | H | H | $CH_3$ | S | H | $OCH_3$ | |
| H | H | H | $CH_3$ | O | $CH_3$ | $CH_3$ | |
| H | H | H | $CH_3$ | O | $CH_3$ | $CH_3$ | |
| H | H | H | $CH_3$ | O | $CH_3$ | $OCH_3$ | |
| H | H | H | $CH_3$ | O | $CH_3$ | $OCH_3$ | |
| H | H | H | $CH_3$ | O | $OCH_3$ | $CH_3$ | |
| H | H | H | $CH_3$ | O | $OCH_3$ | $CH_3$ | |
| H | H | H | $CH_3$ | O | $OCH_3$ | $OCH_3$ | |
| H | H | H | $CH_3$ | O | $OCH_3$ | $OCH_3$ | |
| H | H | H | $CH_3$ | O | H | $OC_2H_5$ | |
| H | H | H | $CH_3$ | O | H | $OC_2H_5$ | |
| H | H | H | $-CH_2-(CH_2)_4CH_3$ | O | H | $OCH_3$ | |
| H | H | H | $CH_2-CH=CH-CH_3$ | O | H | $CH_3$ | |
| H | H | H | cyclopropyl | O | H | $OCH_3$ | |
| H | H | H | 4-F-phenyl | O | H | $OCH_3$ | |
| H | H | H | 4-CN-phenyl | O | H | $OCH_3$ | |
| H | H | H | 3-Br-phenyl-CH(CH₃)₂ | O | H | $OCH_3$ | |
| H | H | H | 4-$SO_2CH_3$-phenyl | O | H | $OCH_3$ | |
| H | H | H | 4-$SCH_3$-phenyl | O | H | $CH_3$ | |

TABLE IXa-continued

| R | $R_1$ | $R_2$ | $R_{12}$ | W | $R_8$ | Y' | m.p. (°C.) |
|---|---|---|---|---|---|---|---|
| H | H | H | 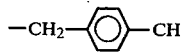 -Cl | O | H | Cl | |
| H | H | H | -CH₂-  -CH₃ | O | H | Cl | |
| H | H | H | -CH₂- 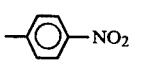 -CH(CH₃)₂ | O | H | OCH₃ | |
| 5-OC₂H₅ | H | H | CH₃ | O | H | OCH₃ | |
| 4-CH(CH₃)₂ | H | H | CH₃ | O | H | OCH₃ | |
| 5-CF₃ | H | H | 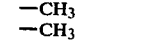 -NO₂ | O | H | OCH₃ | |

TABLE X

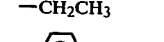

| R | $R_1$ | $R_2$ | $R_{13}$ | W | $R_8$ | X | Y | m.p. (°C.) |
|---|---|---|---|---|---|---|---|---|
| H | H | H | —CH₃ | O | H | CH₃ | CH₃ | |
| H | H | H | —CH₃ | O | H | CH₃ | OCH₃ | |
| H | H | H | —CH₃ | O | H | OCH₃ | OCH₃ | |
| H | H | H | —CH₂CH₃ | O | H | CH₃ | OCH₃ | |
| H | H | H | —CH₂CH₃ | O | H | OCH₃ | OCH₃ | |
| H | H | H | 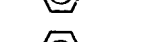 | O | H | CH₃ | OCH₃ | |
| H | H | H |  | O | H | OCH₃ | OCH₃ | |
| H | H | H | —⟨◯⟩—Cl | O | H | CH₃ | OCH₃ | |
| H | H | H | —⟨◯⟩—Cl | O | H | OCH₃ | OCH₃ | |
| H | H | CH₃ | CH₃ | O | H | OCH₃ | OCH₃ | |
| H | CH₃ | CH₃ | CH₃ | O | H | OCH₃ | OCH₃ | |
| 5-F | H | H | CH₃ | O | H | OCH₃ | OCH₃ | |
| 5-Cl | H | H | CH₃ | O | H | OCH₃ | OCH₃ | |
| 5-CH₃ | H | H | CH₃ | O | H | OCH₃ | OCH₃ | |
| 3-NO₂ | H | H | CH₃ | O | H | OCH₃ | OCH₃ | |
| 5-OCH₃ | H | H | CH₃ | O | H | OCH₃ | OCH₃ | |
| 5-CF₃ | H | H | CH₃ | O | H | OCH₃ | OCH₃ | |
| 5-Cl | H | H | CH₃ | O | H | CH₃ | OCH₃ | |
| 6-Cl | H | H | CH₃ | O | H | CH₃ | OCH₃ | |
| H | H | H | CH₃ | O | H | Cl | Cl | |
| H | H | H | CH₃ | O | H | Cl | OCH₃ | |
| H | H | H | CH₃ | O | H | Br | OCH₃ | |
| H | H | H | CH₃ | O | H | CH₂CH₃ | OCH₃ | |
| H | H | H | CH₃ | O | H | OCH₂CH₃ | CH₃ | |
| H | H | H | CH₃ | O | H | OCH(CH₃)₂ | CH₃ | |
| H | H | H | CH₃ | O | H | CF₃ | OCH₃ | |

TABLE X-continued

| R | R₁ | R₂ | R₁₃ | W | R₈ | X | Y | m.p. (°C.) |
|---|---|---|---|---|---|---|---|---|
| H | H | H | CH₃ | O | H | SCH₃ | OCH₃ | |
| H | H | H | CH₃ | O | H | CH₂OCH₃ | CH₃ | |
| H | H | H | CH₃ | O | H | CH₂OCH₃ | OCH₃ | |
| H | H | H | CH₃ | O | H | H | CH₃ | |
| H | H | H | CH₃ | O | H | H | OCH₃ | |
| H | H | H | —⌬ | O | H | Cl | Cl | |
| H | H | H | —⌬ | O | H | OCH₃ | OCH₃ | |
| 4-CH₃ | H | H | CH₃ | O | H | OCH₃ | OCH₃ | |
| 5-OC₂H₅ | H | H | CH₃ | O | H | OCH₃ | OCH₃ | |
| 4-CH(CH₃)₂ | H | H | CH₃ | O | H | OCH₃ | OCH₃ | |
| H | H | H | CH₂(CH₂)₄CH₃ | O | H | OCH₃ | OCH₃ | |
| H | H | H | CH₂CH₂CH₃ | O | H | OCH₃ | OCH₃ | |
| 4-CF₃ | H | H | CH₃ | O | H | OCH₃ | OCH₃ | |
| H | H | H | CH₃ | O | H | Cl | OCH₃ | |
| 6-C₂H₅ | H | H | CH₃ | O | H | Cl | Cl | |
| H | H | H | —⌬—CH₃ | O | H | OCH₃ | OCH₃ | |
| H | H | H | CH₃ | S | H | CH₃ | CH₃ | |
| H | H | H | CH₃ | S | H | CH₃ | OCH₃ | |
| H | H | H | CH₃ | S | H | OCH₃ | OCH₃ | |
| H | H | H | CH₃ | S | CH₃ | CH₃ | CH₃ | |
| H | H | H | CH₃ | S | CH₃ | CH₃ | OCH₃ | |
| H | H | H | CH₃ | S | CH₃ | OCH₃ | OCH₃ | |
| H | H | H | CH₃ | S | OCH₃ | CH₃ | CH₃ | |
| H | H | H | CH₃ | S | OCH₃ | CH₃ | OCH₃ | |
| H | H | H | CH₃ | S | OCH₃ | OCH₃ | OCH₃ | |

TABLE XI

| R | R₁ | R₂ | R₁₃ | W | R₈ | X | Y | Z | m.p. (°C.) |
|---|---|---|---|---|---|---|---|---|---|
| H | H | H | —CH₃ | O | H | CH₃ | CH₃ | CH | |
| H | H | H | —CH₃ | O | H | CH₃ | OCH₃ | CH | |
| H | H | H | —CH₃ | O | H | OCH₃ | OCH₃ | CH | |
| H | H | H | —CH₂CH₃ | O | H | CH₃ | OCH₃ | CH | |
| H | H | H | —CH₂CH₃ | O | H | OCH₃ | OCH₃ | CH | |
| H | H | H | —⌬—Cl | O | H | CH₃ | CH₃ | CH | |
| H | H | H | —⌬ | O | H | CH₃ | OCH₃ | CH | |
| H | H | H | —⌬ | O | H | OCH₃ | OCH₃ | CH | |
| H | H | H | —⌬—Cl | O | H | CH₃ | OCH₃ | CH | |

TABLE XI-continued

| R | R₁ | R₂ | R₁₃ | W | R₈ | X | Y | Z | m.p. (°C.) |
|---|---|---|---|---|---|---|---|---|---|
| H | H | H | -⟨C₆H₄⟩-Cl | O | H | OCH₃ | OCH₃ | CH | |
| H | H | CH₃ | CH₃ | O | H | OCH₃ | OCH₃ | CH | |
| H | CH₃ | CH₃ | CH₃ | O | H | OCH₃ | OCH₃ | CH | |
| 5-F | H | H | CH₃ | O | H | OCH₃ | OCH₃ | CH | |
| 4-Cl | H | H | CH₃ | O | H | OCH₃ | OCH₃ | CH | |
| 5-CH₃ | H | H | CH₃ | O | H | OCH₃ | OCH₃ | CH | |
| 5-NO₂ | H | H | CH₃ | O | H | OCH₃ | OCH₃ | CH | |
| 5-OCH₃ | H | H | CH₃ | O | H | OCH₃ | OCH₃ | CH | |
| 5-CF₃ | H | H | CH₃ | O | H | OCH₃ | OCH₃ | CH | |
| 5-Cl | H | H | CH₃ | O | H | CH₃ | OCH₃ | CH | |
| 6-Cl | H | H | CH₃ | O | H | CH₃ | OCH₃ | CH | |
| H | H | H | CH₃ | O | H | Cl | Cl | CH | |
| H | H | H | CH₃ | O | H | Cl | OCH₃ | CH | |
| H | H | H | CH₃ | O | H | Br | OCH₃ | CH | |
| H | H | H | CH₃ | O | H | CH₂CH₃ | OCH₃ | CH | |
| H | H | H | CH₃ | O | H | OCH₂CH₃ | CH₃ | CH | |
| H | H | H | CH₃ | O | H | OCH(CH₃)₂ | CH₃ | CH | |
| H | H | H | CH₃ | O | H | CF₃ | OCH₃ | CH | |
| H | H | H | CH₃ | O | H | SCH₃ | OCH₃ | CH | |
| H | H | H | CH₃ | O | H | CH₂OCH₃ | CH₃ | CH | |
| H | H | H | CH₃ | O | H | CH₂OCH₃ | OCH₃ | CH | |
| H | H | H | CH₃ | O | H | H | CH₃ | CH | |
| H | H | H | CH₃ | O | H | H | OCH₃ | CH | |
| H | H | H | CH₃ | O | H | Cl | Cl | CH | |
| H | H | H | -⟨C₆H₅⟩ | O | H | OCH₃ | OCH₃ | CH | |
| H | H | H | CH₃ | O | H | H | CH₃ | CCl | |
| H | H | H | CH₃ | O | H | CH₃ | CH₃ | C—CN | |
| H | H | H | CH₃ | O | H | CH₃ | CH₃ | CCH₃ | |
| H | H | H | CH₃ | O | H | H | CH₃ | CCH₃ | |
| H | H | H | CH₃ | O | H | CH₃ | CH₃ | CCH₂CH₃ | |
| H | H | H | CH₃ | O | H | H | CH₃ | CCH₂CH₃ | |
| H | H | H | CH₃ | O | H | Cl | Cl | C—CH₂CH₂Cl | |
| H | H | H | CH₃ | O | H | H | CH₃ | C—CH₂CH₂Cl | |
| H | H | H | CH₃ | O | H | CH₃ | CH₃ | C—CH₂CH₂Cl | |
| H | H | H | CH₃ | O | H | CH₃ | CH₃ | C—CH₂CH=CH₂ | |
| H | H | H | CH₃ | O | H | H | CH₃ | C—CH₂CH=CH₂ | |
| 5-OC₂H₅ | H | H | CH₃ | O | H | OCH₃ | OCH₃ | CH | |
| 5-CH(CH₃)₂ | H | H | CH₃ | O | H | OCH₃ | OCH₃ | CH | |
| 4-CF₃ | H | H | CH₃ | O | H | OCH₃ | OCH₃ | CH | |
| H | H | H | CH₂(CH₂)₄CH₃ | O | H | OCH₃ | OCH₃ | CH | |
| H | H | H | CH₂CH₂CH₃ | O | H | OCH₃ | CH₃ | CH | |
| H | H | H | CH₃ | O | H | Cl | Cl | CH | |
| 6-C₂H₅ | H | H | CH₃ | O | H | Cl | Cl | CH | |
| H | H | H | -⟨C₆H₄⟩-CH₃ | O | H | OCH₃ | OCH₃ | CH | |
| H | H | H | CH₃ | S | H | CH₃ | CH₃ | CH | |
| H | H | H | CH₃ | S | H | CH₃ | OCH₃ | CH | |
| H | H | H | CH₃ | S | H | OCH₃ | OCH₃ | CH | |
| H | H | H | CH₃ | O | CH₃ | CH₃ | CH₃ | CH | |
| H | H | H | CH₃ | O | CH₃ | CH₃ | OCH₃ | CH | |
| H | H | H | CH₃ | O | CH₃ | OCH₃ | OCH₃ | CH | |
| H | H | H | CH₃ | O | OCH₃ | CH₃ | CH₃ | CH | |
| H | H | H | CH₃ | O | OCH₃ | CH₃ | OCH₃ | CH | |
| H | H | H | CH₃ | O | OCH₃ | OCH₃ | OCH₃ | CH | |

TABLE XII

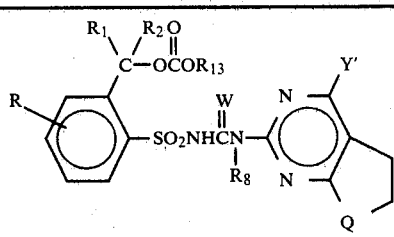

| R | $R_1$ | $R_2$ | $R_{13}$ | W | $R_8$ | Y' | Q | m.p. (°C.) |
|---|---|---|---|---|---|---|---|---|
| H | H | H | —$CH_3$ | O | H | $CH_3$ | O | |
| H | H | H | —$CH_3$ | O | H | $OCH_3$ | O | |
| H | H | H | —$CH_2CH_3$ | O | H | $CH_3$ | O | |
| H | H | H | phenyl | O | H | $CH_3$ | O | |
| H | H | H | phenyl | O | H | $OCH_3$ | O | |
| H | H | H | 4-Cl-phenyl | O | H | $OCH_3$ | O | |
| H | H | $CH_3$ | $CH_3$ | O | H | $OCH_3$ | O | |
| H | $CH_3$ | $CH_3$ | $CH_3$ | O | H | $OCH_3$ | O | |
| 5-F | H | H | $CH_3$ | O | H | $OCH_3$ | O | |
| 5-Cl | H | H | $CH_3$ | O | H | $OCH_3$ | O | |
| 3-$CH_3$ | H | H | $CH_3$ | O | H | $OCH_3$ | O | |
| 5-$NO_2$ | H | H | $CH_3$ | O | H | $OCH_3$ | O | |
| 5-$OCH_3$ | H | H | $CH_3$ | O | H | $OCH_3$ | O | |
| 4-$CF_3$ | H | H | $CH_3$ | O | H | $OCH_3$ | O | |
| 5-Cl | H | H | $CH_3$ | O | H | $CH_3$ | O | |
| 6-Cl | H | H | $CH_3$ | O | H | $CH_3$ | O | |
| H | H | H | $CH_3$ | O | H | H | O | |
| H | H | H | $CH_3$ | O | H | H | $CH_2$ | |
| H | H | H | $CH_3$ | O | H | Cl | $CH_2$ | |
| H | H | H | $CH_3$ | O | H | $CH_3$ | $CH_2$ | |
| H | H | H | $CH_3$ | O | H | $OCH_3$ | $CH_2$ | |
| 5-$OC_2H_5$ | H | H | $CH_3$ | O | H | $OCH_3$ | O | |
| 4-CH(CH_3)_2 | H | H | $CH_3$ | O | H | $OCH_3$ | O | |
| 6-$CH_3$ | H | H | $CH_3$ | O | H | $OCH_3$ | O | |
| 4-$CF_3$ | H | H | $CH_3$ | | | $OCH_3$ | O | |
| H | H | H | $CH_2(CH_2)_4CH_3$ | O | H | $OCH_3$ | O | |
| H | H | H | —$CH_2CH_2CH_3$ | O | H | $OCH_3$ | O | |
| H | H | H | 4-$CH_3$-phenyl | O | H | $OCH_3$ | O | |
| H | H | H | 4-Cl-phenyl | O | H | $CH_3$ | O | |
| H | H | H | 2-Cl-phenyl | O | H | $OCH_3$ | O | |
| H | H | H | $CH_3$ | S | H | $CH_3$ | O | |
| H | H | H | $CH_3$ | S | H | $OCH_3$ | O | |
| H | H | H | $CH_3$ | S | H | $CH_3$ | $CH_2$ | |
| H | H | H | $CH_3$ | S | H | $OCH_3$ | $CH_2$ | |
| H | H | H | $CH_3$ | O | $CH_3$ | $CH_3$ | O | |
| H | H | H | $CH_3$ | O | $CH_3$ | $CH_3$ | $CH_2$ | |
| H | H | H | $CH_3$ | O | $CH_3$ | $OCH_3$ | O | |
| H | H | H | $CH_3$ | O | $CH_3$ | $OCH_3$ | $CH_2$ | |
| H | H | H | $CH_3$ | O | $OCH_3$ | $CH_3$ | O | |
| H | H | H | $CH_3$ | O | $OCH_3$ | $CH_3$ | $CH_2$ | |
| H | H | H | $CH_3$ | O | $OCH_3$ | $OCH_3$ | O | |
| H | H | H | $CH_3$ | O | $OCH_3$ | $OCH_3$ | $CH_2$ | |
| H | H | H | $CH_3$ | O | H | $OC_2H_5$ | O | |
| H | H | H | $CH_3$ | O | H | $OC_2H_5$ | $CH_2$ | |

TABLE XIIa

Structure: R-phenyl with substituent $-C(R_1)(R_2)-OC(=O)OR_{13}$ (ortho) and $-SO_2NHC(=W)N(R_8)-$ pyrimidine ring fused to dihydrofuran/pyran with Y' substituent.

| R | $R_1$ | $R_2$ | $R_{13}$ | W | $R_8$ | Y' | m.p. (°C.) |
|---|---|---|---|---|---|---|---|
| H | H | H | —CH₃ | O | H | CH₃ | |
| H | H | H | —CH₃ | O | H | OCH₃ | |
| H | H | H | —CH₂CH₃ | O | H | CH₃ | |
| H | H | H | —C₆H₅ (phenyl) | O | H | CH₃ | |
| H | H | H | —C₆H₅ (phenyl) | O | H | OCH₃ | |
| H | H | H | —C₆H₄Cl | O | H | OCH₃ | |
| H | H | CH₃ | CH₃ | O | H | OCH₃ | |
| H | CH₃ | CH₃ | CH₃ | O | H | OCH₃ | |
| 5-F | H | H | CH₃ | O | H | OCH₃ | |
| 5-Cl | H | H | CH₃ | O | H | OCH₃ | |
| 3-CH₃ | H | H | CH₃ | O | H | OCH₃ | |
| 5-NO₂ | H | H | CH₃ | O | H | OCH₃ | |
| 5-OCH₃ | H | H | CH₃ | O | H | OCH₃ | |
| 4-CF₃ | H | H | CH₃ | O | H | OCH₃ | |
| 5-Cl | H | H | CH₃ | O | H | CH₃ | |
| 6-Cl | H | H | CH₃ | O | H | CH₃ | |
| H | H | H | CH₃ | O | H | H | |
| H | H | H | CH₃ | O | H | H | |
| H | H | H | CH₃ | O | H | Cl | |
| H | H | H | CH₃ | O | H | CH₃ | |
| H | H | H | CH₃ | O | H | OCH₃ | |
| 5-OC₂H₅ | H | H | CH₃ | O | H | OCH₃ | |
| 4-CH(CH₃)₂ | H | H | CH₃ | O | H | OCH₃ | |
| 6-CH₃ | H | H | CH₃ | O | H | OCH₃ | |
| 4-CF₃ | H | H | CH₃ | | | OCH₃ | |
| H | H | H | CH₂(CH₂)₄CH₃ | O | H | OCH₃ | |
| H | H | H | —CH₂CH₂CH₃ | O | H | OCH₃ | |
| H | H | H | —C₆H₄CH₃ | O | H | OCH₃ | |
| H | H | H | —C₆H₄Cl | O | H | CH₃ | |
| H | H | H | —C₆H₄Cl (o-Cl) | O | H | OCH₃ | |
| H | H | H | CH₃ | S | H | CH₃ | |
| H | H | H | CH₃ | S | H | OCH₃ | |
| H | H | H | CH₃ | S | H | CH₃ | |
| H | H | H | CH₃ | S | H | OCH₃ | |
| H | H | H | CH₃ | O | CH₃ | CH₃ | |
| H | H | H | CH₃ | O | CH₃ | CH₃ | |
| H | H | H | CH₃ | O | CH₃ | OCH₃ | |
| H | H | H | CH₃ | O | CH₃ | OCH₃ | |
| H | H | H | CH₃ | O | OCH₃ | CH₃ | |
| H | H | H | CH₃ | O | OCH₃ | CH₃ | |
| H | H | H | CH₃ | O | OCH₃ | OCH₃ | |
| H | H | H | CH₃ | O | OCH₃ | OCH₃ | |
| H | H | H | CH₃ | O | H | OC₂H₅ | |
| H | H | H | CH₃ | O | H | OC₂H₅ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XIII

|  | Active* Ingredient | Diluent (s) | Surfactant (s) |
|---|---|---|---|
| Wettable Powders | 20–90 | 0–74 | 1–10 |
| Oil Suspensions, Emulsions, Solutions (including Emulsifiable Concentrates | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, March 14, 1967, Col. 5, line 43 through Col. 1, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, June 23, 1959, Col. 5, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 8

Wettable Powder

| | |
|---|---|
| N-[(4,6-Dimethoxypyrimidin-2-yl)aminocarbonyl]-2-(hydroxymethyl)-benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended and packaged.

EXAMPLE 9

Wettable Powder

| | |
|---|---|
| N-[(4-6-Dimethoxy-1,3,5-triazin-2-yl)aminocarbonyl]-2-(hydroxymethyl)-benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of essentially all below 10 microns in diameter. The product is reblended before packaging.

EXAMPLE 10

Granule

| | |
|---|---|
| wettable powder of Example 9 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 11

Extruded Pellet

| | |
|---|---|
| N-[(4,6-Dimethoxypyrimidin-2-yl)aminocarbonyl]-2-(hydroxymethyl)-benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

Oil Suspension

| | |
|---|---|
| N-[(4,6-Dimethoxy-1,3,5-triazin-2-yl)amino-carbonyl]-2-(hydroxymethyl)-benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

Wettable Powder

| | |
|---|---|
| N-[(4,5-Dimethoxypyrimidin-2-yl)amino-carbonyl]-2-(hydroxymethyl)-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 14

Low Strength Granule

| | |
|---|---|
| N-[(4,6-Dimethoxy-1,3,5-triazin-2-yl)-aminocarbonyl]-2-(hydroxymethyl)-benzenesulfonamide | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

Aqueous Suspension

| | |
|---|---|
| N-[(4,6-Dimethoxypyrimidin-2-yl)-aminocarbonyl]-2-(hydroxymethyl)-benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 16

Solution

| | |
|---|---|
| N-[(4,6-Dimethoxypyrimidin-2-yl)-aminocarbonyl]-2-(hydroxymethyl)-benzenesulfonamide, sodium salt | 5% |
| water | 95% |

The salt is added directly to the water with stirring to produce the solution, which may then be packaged for use.

EXAMPLE 17

Low Strength Granule

| | |
|---|---|
| N-[(4,6-Dimethoxypyrimidin-2-yl)-aminocarbonyl]-2-(hydroxymethyl)-benzenesulfonamide | 0.1% |
| attapulgite granules (U.S.S. 20–40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 18

Granule

| | |
|---|---|
| N-[(4,6-Dimethoxy-1,3,5-triazin-2-yl)-aminocarbonyl]-2-(hydroxymethyl)-benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 19

High Strength Concentrate

| | |
|---|---|
| N-[(4,6-Dimethoxypyrimidin-2-yl)-aminocarbonyl]-2-(hydroxymethyl)-benzenesulfonamide | 99% |
| silica aerogel | 0.5% |
| synthetic amorphous silica | 0.5% |

The ingredients are blended and ground in a hammer-mill to produce a material essentially all passing a U.S.S.

No. 50 screen (0.3 mm opening). The concentrate may be formulated further if necessary.

EXAMPLE 20

Wettable Powder

| | |
|---|---|
| N-[(4,6-Dimethoxy-1,3,5-triazin-2-yl)-aminocarbonyl]-2-(hydroxymethyl)-benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 21

Wettable Powder

| | |
|---|---|
| N-[(4,6-Dimethoxy-1,3,5-triazin-2-yl)-aminocarbonyl]-2-(hydroxymethyl)-benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

Oil Suspension

| | |
|---|---|
| N-[(4,6-Dimethoxy-1,3,5-triazin-2-yl)-aminocarbonyl]-2-(hydroxymethyl)-benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are active herbicides. They have utility for broadspectrum pre- and/or post-emergence weed control in areas where complete control of all vegetation is desired, such as around fuel storage tanks, ammunition depots, industrial storage, areas, oil well sites, drive-in theaters, around billboards, highway and railroad structures. By properly selecting rate and time of application, compounds of this invention may be used to modify plant growth beneficially, and also selectively control weeds in crops such as wheat.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.05 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-(isopropylamino)-s-triazine (atrazine); the uracils such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamide); 2,4-dichlorophenoxyacetic acid (2,4-d) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); $\alpha,\alpha,\alpha$-trifluoro-2,6-dinitro-N,N-dipropyl-p-toluidine (trifluralin); 1,1'-dimethyl-4,4'-bipyridinium ion (paraquat); 2-chloro-2',6'-diethyl(methoxymethyl)acetanilide (alachlor); 1,1-dimethyl-3-($\alpha,\alpha,\alpha$-trifluoro-m-tolyl)urea (fluometuron); S-(4-chlorobenzyl)N,N-diethylthiolcarbamate (benthiocarb); N-(butoxymethyl)-2-chloro-2',6'-diethylacetanilide (butachlor); and 5-[2-chloro-5-(trifluoromethyl)phenoxy]-2-nitrobenzoic acid, methyl ester (acifluorfen-methyl).

Test Procedure A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium spp.), sorghum, corn, soybean, rice, wheat and nutsedge tubers (Cyperus rotundus) were planted in a growth medium and treated preemergence with the chemicals dissolved in a nonphytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three to five leaves were sprayed. Treated plants and controls were maintained in a greenhouse for 16 days, then all species were compared to controls and visually rated for response to treatment.

Ratings for compounds tested by this procedure are recorded in Table XIV.

0=no effect
10=maximum effect
C=chlorosis or necrosis
D=defoliation
E=emergence inhibition
G=growth retardation
H=formative effects
6Y=abscised buds or flowers.

TABLE XIV

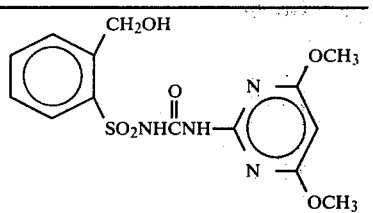

| kg/ha | 0.05 |
|---|---|
| POST-EMERGENCE | |
| BUSH BEAN | 5C, 10D, 6Y |
| COTTON | 3C, 4H, 8G |
| MORNINGGLORY | 2G |
| COCKLEBUR | 5C, 9G |
| CASSIA | 5C, 9G |
| NUTSEDGE | 1C, 9G |
| CRABGRASS | 3G |
| BARNYARDGRASS | 3C, 9H |
| WILD OATS | 1C, 3G |
| WHEAT | 0 |
| CORN | 2C, 9H |
| SOYBEAN | 9C |
| RICE | 2C, 9G |
| SORGHUM | 2C, 9H |
| | |
| PRE-EMERGENCE | |
| MORNINGGLORY | 8G |
| COCKLEBUR | 9H |
| CASSIA | 1C, 8G |
| NUTSEDGE | 10E |
| CRABGRASS | 2C |
| BARNYARDGRASS | 2C, 9H |
| WILD OATS | 8G, O |
| WHEAT | 6G, O |
| CORN | 1C, 9H |
| SOYBEAN | 2C, 8H |
| RICE | 10E |
| SORGHUM | 2C, 9G |

TABLE XV

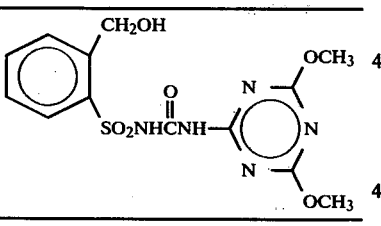

| kg/ha | 0.05 |
|---|---|
| POST-EMERGENCE | |
| BUSHBEAN | 2C, 7G, 6Y |
| COTTON | 0 |
| MORNINGGLORY | 1C |
| COCKLEBUR | 0 |
| CASSIA | 1C |
| NUTSEDGE | 0 |
| CRABGRASS | 2G |
| BARNYARDGRASS | 0 |
| WILD OATS | 0 |
| WHEAT | 0 |
| CORN | 2C, 9H |
| SOYBEAN | 1C, 6H |
| RICE | 1C, 4G |
| SORGHUM | 2C, 9H |
| | |
| PRE-EMERGENCE | |
| MORNINGGLORY | 2C |
| COCKLEBUR | 0 |
| CASSIA | 1C |
| NUTSEDGE | 0 |
| CRABGRASS | 0 |
| BARNYARDGRASS | 2C, 7H |
| WILD OATS | 0 |
| WHEAT | 0 |
| CORN | 9H |

TABLE XV-continued

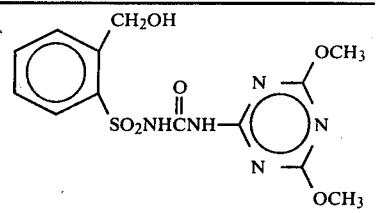

| SOYBEAN | 2C, 3H |
|---|---|
| RICE | 1C |
| SORGHUM | 2C, 9H |

What is claimed is:

1. A compound selected from

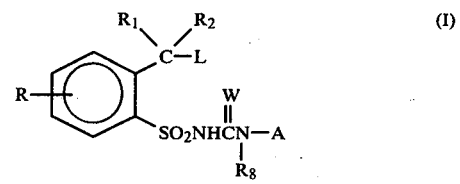

wherein

L is OH, OC(O)R$_{11}$, OC(O)NHR$_{12}$ or OC(O)OR$_{13}$;

R is H, F, Cl, Br, NO$_2$, CF$_3$, C$_1$–C$_3$ alkyl or C$_1$–C$_3$ alkoxy;

R$_1$ is H or C$_1$–C$_4$ alkyl;

R$_2$ is H or CH$_3$;

R$_8$ is H, CH$_3$ or OCH$_3$;

R$_{11}$ is H, C$_1$–C$_5$ alkyl, C$_2$–C$_3$ alkenyl, C$_2$–C$_3$ alkynyl, C$_3$–C$_4$ cycloalkyl,

C$_1$–C$_4$ alkyl substituted with 1–4 substituents selected from 0–3 F, 0–3 Cl or 0–3 Br or C$_2$–C$_3$ alkenyl substituted with 1–3 Cl;

R$_{12}$ is H, C$_1$–C$_6$ alkyl, C$_3$–C$_4$ alkenyl, C$_5$–C$_6$ cycloalkyl,

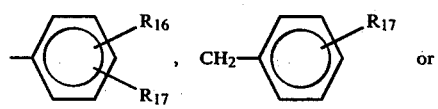

C$_5$–C$_6$ cycloalkyl substituted with CH$_3$;

R$_{13}$ is C$_1$–C$_6$ alkyl or

R$_{14}$ and R$_{15}$ are independently H, NO$_2$, CH$_3$, Cl or OCH$_3$;

R$_{16}$ is H, F, Cl, Br, C$_1$–C$_3$ alkyl, NO$_2$, CN, SO$_2$CH$_3$, OCH$_3$, SCH$_3$ or CF$_3$;

R$_{17}$ is H, Cl or C$_1$–C$_3$ alkyl;

R$_{18}$ is H, CH$_3$ or Cl;

A is

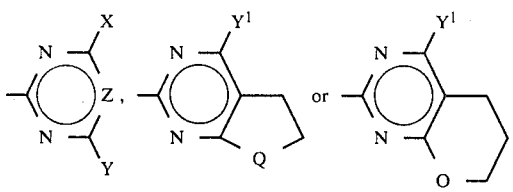

W is O or S;

X is H, Cl, Br, CH$_3$, CH$_2$CH$_3$, C$_1$-C$_3$ alkoxy, CF$_3$, SCH$_3$ or CH$_2$OCH$_3$;

Y is CH$_3$ or OCH$_3$;

Z is N, CH, CCl, CBr, CCN, CCH$_3$, CCH$_2$CH$_3$, CCH$_2$CH$_2$Cl or CCH$_2$CH=CH$_2$;

Y$^1$ is H, CH$_3$, OCH$_3$ or OCH$_2$CH$_3$; and

Q is O or CH$_2$;

and their agriculturally suitable salts; provided that when W is S, then R$_8$ is H.

2. A compound of claim 1 where Z is N, CH, CCl, CBr or CCH$_3$, W is O and R$_8$ is H or CH$_3$.

3. A compound of claim 1 where L is OH; R is H; R$_1$ and R$_2$ are CH$_3$; and R$_8$ is H or CH$_3$; A is

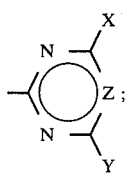

Z is CH or N; X and Y are independently CH$_3$ or OCH$_3$; and W is O.

4. A compound of claim 2 where Z is CH or N; X is CH$_3$ or OCH$_3$; and R$_1$ is H or CH$_3$.

5. A compound of claim 4 where R and R$_8$ are H, and A is

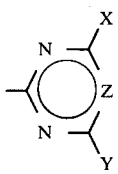

6. A compound of claim 5 where R$_{11}$, R$_{12}$ and R$_{13}$ are C$_1$-C$_3$ alkyl.

7. A compound of claim 5 where L is OH.

8. The compound of claim 1, N-[(4,6-dimethoxypyrimidin-2-yl)aminocarbonyl]-2-(hydroxymethyl)-benzenesulfonamide.

9. The compound of claim 1, N-[(4,6-dimethoxy-1,3,5-triazin-2-yl)aminocarbonyl]-2-(hydroxymethyl)-benzenesulfonamide.

10. The compound of claim 1, N-[(4,6-dimethylpyrimidin-2-yl)aminocarbonyl]-2-(hydroxymethyl)benzenesulfonamide.

11. The compound of claim 1, N-[(4-methoxy-6-methylpyrimidin-2-yl)aminocarbonyl]-2-(hydroxymethyl)benzenesulfonamide.

12. The compound of claim 1, N-[(4,6-dimethyl-1,3,5-triazin-2-yl)aminocarbonyl]-2-(hydroxymethyl)benzenesulfonamide.

13. The compound of claim 1, N-[(4-methoxy-6-methyl-1,3,5-triazin-2-yl)aminocarbonyl]-2-(hydroxymethyl)benzenesulfonamide.

14. A composition for the control of undesirable vegetation consisting essentially of a compound of claim 1 and at least one of (a) a surface-active agent and (b) a solid or liquid diluent.

15. A composition for the control of undesirable vegetation consisting essentially of a compound of claim 2 and at least one of (a) a surface-active agent and (b) a solid or liquid diluent.

16. A composition for the control of undesirable vegetation consisting essentially of a compound of claim 3 and at least one of (a) a surface-active agent and (b) a solid or liquid diluent.

17. A composition for the control of undesirable vegetation consisting essentially of a compound of claim 4 and at least one of (a) a surface-active agent and (b) a solid or liquid diluent.

18. A composition for the control of undesirable vegetation consisting essentially of a compound of claim 5 and at least one of (a) a surface-active agent and (b) a solid or liquid diluent.

19. A composition for the control of undesirable vegetation consisting essentially of a compound of claim 6 and at least one of (a) a surface-active agent and (b) a solid or liquid diluent.

20. A method for the control of undesirable vegetation consisting of applying to the locus of such undesirable vegetation a herbicidally effective amount of a compound of claim 1.

21. A method for the control of undesirable vegetation comprising applying to the locus of such undesirable vegetation a herbicidally effective amount of a compound of claim 2.

22. A method for the control of undesirable vegetation comprising applying to the locus of such undesirable vegetation a herbicidally effective amount of a compound of claim 3.

23. A method for the control of undesirable vegetation comprising applying to the locus of such undesirable vegetation a herbicidally effective amount of a compound of claim 4.

24. A method for the control of undesirable vegetation comprising applying to the locus of such undesirable vegetation a herbicidally effective amount of the compound of claim 5.

25. A method for the control of undesirable vegetation comprising applying to the locus of such undesirable vegetation a herbicidally effective amount of the compound of claim 6.

* * * * *